United States Patent [19]

Khandke et al.

[11] Patent Number: 5,741,692

[45] Date of Patent: Apr. 21, 1998

[54] PROTEIN VULGARIS CHONDROITINASE II

[75] Inventors: Kiran M. Khandke, Nanuet; John Gotto, Suffern, both of N.Y.; Ursula Eul, Kahl, Germany

[73] Assignee: American Cyanamid Company, Wayne, N.J.

[21] Appl. No.: 428,948

[22] Filed: Apr. 24, 1995

Related U.S. Application Data

[63] Continuation-in-part of Ser. No. 231,534, Apr. 22, 1994, Pat. No. 5,525,500, and a continuation-in-part of Ser. No. 232,540, Apr. 22, 1994, Pat. No. 5,498,536.

[51] Int. Cl.⁶ .............. C12N 9/24; C12N 9/26; C12N 9/28; C12N 1/00; C12N 1/12
[52] U.S. Cl. .............. 435/200; 435/201; 435/202; 435/873; 435/252.1
[58] Field of Search .............. 435/200, 201, 435/202, 873, 252.1

[56] References Cited

U.S. PATENT DOCUMENTS

| | | | |
|---|---|---|---|
| 4,696,816 | 9/1987 | Brown | 424/94 |
| 5,049,501 | 9/1991 | Katsuragi et al. | 435/199 |
| 5,198,355 | 3/1993 | Kikuchi et al. | 435/232 |
| 5,292,509 | 3/1994 | Hageman | 424/94.61 |
| 5,496,718 | 3/1996 | Hashimoto et al. | 435/232 |
| 5,498,536 | 3/1996 | Khandke | 435/200 |
| 5,525,500 | 6/1996 | Khandke et al. | 435/232 |

FOREIGN PATENT DOCUMENTS

| | | |
|---|---|---|
| 0 576 294 A2 | 12/1993 | European Pat. Off. . |
| 0 613 949 A2 | 9/1994 | European Pat. Off. . |
| 62-122588 | 6/1987 | Japan . |
| 1067253 | 5/1967 | United Kingdom . |
| 94/25567 | 11/1994 | WIPO . |

OTHER PUBLICATIONS

Kitamikado et al., *Applied Microbiology*, 29:414–421, 1975.
Sato et al., *Applied Microbiology Biotechnol.*, 41:39–46, 1994.
Sato et al., *Agric. Biol. Chem.*, 50:1057–1059, 1986.
Yamagata et al. *J. Biol. Chem.*, 243:1523–1535, 1968.
Glover, D.M., (1985), "DNA Cloning, vol. 1, A Practical Approach", pp. 49–77, IRL Press (Oxford).
Scopes (1982) Protein Purification. New York: Springer Verlag. pp. 197–199.
Guthrie et al., *J. Bacteriology* 164:510–515.
Studier et al. (1990), *Methods in Enzymology* 185:60–85.
Lathe (1985), *J. Mol. Biol.* 183:1–11.
Bowie et al. (1990), *Science* 247:1306–1310.

*Primary Examiner*—Jon P. Weber
*Attorney, Agent, or Firm*—Darby & Darby

[57] ABSTRACT

Chondroitinase II, a protein having an isoelectric point of approximately 8.4–8.45 and an apparent molecular mass of 112 kDa when electrophoresed in a 4 to 20% gradient acrylamide gel in 25 mM Tris/192 mM glycine buffer at pH 8.5 in the presence of about 0.1% (w/v) SDS, has been isolated and purified. A process for the copurification by affinity chromatography of the chondroitinase I and chondroitinase II proteins produced by *Proteus vulgaris* is also provided. The proteins can be further purified by metal chelating chromatography. Therapeutic or surgical compositions of isolated chondroitinases I and II or the copurified mixture of chondroitinase I and II are also disclosed. These compositions are used in a method for selectively and completely disinserting the vitreous body from the neural retina of an eye.

4 Claims, 10 Drawing Sheets

LANE A – UNFRACTIONATED CHONDROITINASE
LANES B,C – AFFINITY PURIFIED CHONDROITINASE

Lane A B C D E digest  I  IIa  IIb  IIIa  IIIb  IV

A – PURE 112KDa PROTEIN
B – CO-PURIFIED MIXTURE OF 110KDa AND 112KDa PROTEINS
C – PURIFIED ISOFORM OF CHONDROITINASE (pH 8.45)
D – PURIFIED ISOFORM OF CHONDROITINASE (pH 8.35)
E – I.E.F. STANDARDS

T.L.C. SPOT
    A- CONTROL, PROTEOGLYCAN WITHOUT ENZYME
    B- 112KDa ONLY
    C- 50% EACH OF 112KDa AND 110KDa
    D- 10% OF 112KDa, 90% OF 110KDa
    E- 110KDa ONLY

Chondroitin sulfate, a negatively charged substrate

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 997 amino acids
      ( B ) TYPE: amino acid
      ( D ) TOPOLOGY: linear ( i i ) MOLECULE TYPE: protein ( x i ) SEQUENCE DESCRIPTION: SEQ ID NO:1:

```
Ala  Thr  Ser  Asn  Pro  Ala  Phe  Asp  Pro  Lys  Asn  Leu  Met  Gln  Ser  Glu
 1                    5                        10                       15

Ile  Tyr  His  Phe  Ala  Gln  Asn  Asn  Pro  Leu  Ala  Asp  Phe  Ser  Ser  Asp
               20                        25                       30

Lys  Asn  Ser  Ile  Leu  Thr  Leu  Ser  Asp  Lys  Arg  Ser  Ile  Met  Gly  Asn
          35                        40                       45

Gln  Ser  Leu  Leu  Trp  Lys  Trp  Lys  Gly  Gly  Ser  Ser  Phe  Thr  Leu  His
     50                        55                       60

Lys  Lys  Leu  Ile  Val  Pro  Thr  Asp  Lys  Glu  Ala  Ser  Lys  Ala  Trp  Gly
 65                   70                        75                            80

Arg  Ser  Ser  Thr  Pro  Val  Phe  Ser  Phe  Trp  Leu  Tyr  Asn  Glu  Lys  Pro
                    85                        90                        95

Ile  Asp  Gly  Tyr  Leu  Thr  Ile  Asp  Phe  Gly  Glu  Lys  Leu  Ile  Ser  Thr
              100                       105                      110

Ser  Glu  Ala  Gln  Ala  Gly  Phe  Lys  Val  Lys  Leu  Asp  Phe  Thr  Gly  Trp
          115                       120                      125

Arg  Ala  Val  Gly  Val  Ser  Leu  Asn  Asn  Asp  Leu  Glu  Asn  Arg  Glu  Met
     130                       135                      140

Thr  Leu  Asn  Ala  Thr  Asn  Thr  Ser  Ser  Asp  Gly  Thr  Gln  Asp  Ser  Ile
145                       150                      155                     160

Gly  Arg  Ser  Leu  Gly  Ala  Lys  Val  Asp  Ser  Ile  Arg  Phe  Lys  Ala  Pro
               165                      170                      175

Ser  Asn  Val  Ser  Gln  Gly  Glu  Ile  Tyr  Ile  Asp  Arg  Ile  Met  Phe  Ser
               180                      185                      190

Val  Asp  Asp  Ala  Arg  Tyr  Gln  Trp  Ser  Asp  Tyr  Gln  Val  Lys  Thr  Arg
          195                      200                      205

Leu  Ser  Glu  Pro  Glu  Ile  Gln  Phe  His  Asn  Val  Lys  Pro  Gln  Leu  Pro
     210                      215                      220

Val  Thr  Pro  Glu  Asn  Leu  Ala  Ala  Ile  Asp  Leu  Ile  Arg  Gln  Arg  Leu
225                      230                      235                     240
```

```
Ile Asn Glu Phe Val Gly Gly Glu Lys Glu Thr Asn Leu Ala Leu Glu
            245             250                 255
Glu Asn Ile Ser Lys Leu Lys Ser Asp Phe Asp Ala Leu Asn Ile His
            260             265                 270
Thr Leu Ala Asn Gly Gly Thr Gln Gly Arg His Leu Ile Thr Asp Lys
            275             280                 285
Gln Ile Ile Ile Tyr Gln Pro Glu Asn Leu Asn Ser Gln Asp Lys Gln
            290             295                 300
Leu Phe Asp Asn Tyr Val Ile Leu Gly Asn Tyr Thr Thr Leu Met Phe
305             310                 315                 320
Asn Ile Ser Arg Ala Tyr Val Leu Glu Lys Asp Pro Thr Gln Lys Ala
                325             330                 335
Gln Leu Lys Gln Met Tyr Leu Leu Met Thr Lys His Leu Leu Asp Gln
            340             345                 350
Gly Phe Val Lys Gly Ser Ala Leu Val Thr Thr His His Trp Gly Tyr
            355             360                 365
Ser Ser Arg Trp Trp Tyr Ile Ser Thr Leu Leu Met Ser Asp Ala Leu
    370             375             380
Lys Glu Ala Asn Leu Gln Thr Gln Val Tyr Asp Ser Leu Leu Trp Tyr
385             390             395                 400
Ser Arg Glu Phe Lys Ser Ser Phe Asp Met Lys Val Ser Ala Asp Ser
                405             410                 415
Ser Asp Leu Asp Tyr Phe Asn Thr Leu Ser Arg Gln His Leu Ala Leu
                420             425             430
Leu Leu Leu Glu Pro Asp Asp Gln Lys Arg Ile Asn Leu Val Asn Thr
        435             440                 445
Phe Ser His Tyr Ile Thr Gly Ala Leu Thr Gln Val Pro Pro Gly Gly
    450             455             460
Lys Asp Gly Leu Arg Pro Asp Gly Thr Ala Trp Arg His Glu Gly Asn
465             470             475                 480
Tyr Pro Gly Tyr Ser Phe Pro Ala Phe Lys Asn Ala Ser Gln Leu Ile
                485             490                 495
Tyr Leu Leu Arg Asp Thr Pro Phe Ser Val Gly Glu Ser Gly Trp Asn
            500             505             510
Asn Leu Lys Lys Ala Met Val Ser Ala Trp Ile Tyr Ser Asn Pro Glu
        515             520             525
Val Gly Leu Pro Leu Ala Gly Arg His Pro Phe Asn Ser Pro Ser Leu
    530             535             540
Lys Ser Val Ala Gln Gly Tyr Tyr Trp Leu Ala Met Ser Ala Lys Ser
545             550             555                 560
Ser Pro Asp Lys Thr Leu Ala Ser Ile Tyr Leu Ala Ile Ser Asp Lys
                565             570                 575
Thr Gln Asn Glu Ser Thr Ala Ile Phe Gly Glu Thr Ile Thr Pro Ala
            580             585             590
Ser Leu Pro Gln Gly Phe Tyr Ala Phe Asn Gly Gly Ala Phe Gly Ile
        595             600             605
His Arg Trp Gln Asp Lys Met Val Thr Leu Lys Ala Tyr Asn Thr Asn
    610             615             620
Val Trp Ser Ser Glu Ile Tyr Asn Lys Asp Asn Arg Tyr Gly Arg Tyr
625             630             635                 640
Gln Ser His Gly Val Ala Gln Ile Val Ser Asn Gly Ser Gln Leu Ser
                645             650             655
Gln Gly Tyr Gln Gln Glu Gly Trp Asp Trp Asn Arg Met Gln Gly Ala
            660             665                 670
```

```
Thr  Thr  Ile  His  Leu  Pro  Leu  Lys  Asp  Leu  Asp  Ser  Pro  Lys  Pro  His
          675                680                     685

Thr  Leu  Met  Gln  Arg  Gly  Glu  Arg  Gly  Phe  Ser  Gly  Thr  Ser  Ser  Leu
     690                695                     700

Glu  Gly  Gln  Tyr  Gly  Met  Met  Ala  Phe  Asp  Leu  Ile  Tyr  Pro  Ala  Asn
705                      710                715                           720

Leu  Glu  Arg  Phe  Asp  Pro  Asn  Phe  Thr  Ala  Lys  Lys  Ser  Val  Leu  Ala
                    725                730                          735

Ala  Asp  Asn  His  Leu  Ile  Phe  Ile  Gly  Ser  Asn  Ile  Asn  Ser  Ser  Asp
               740                745                          750

Lys  Asn  Lys  Asn  Val  Glu  Thr  Thr  Leu  Phe  Gln  His  Ala  Ile  Thr  Pro
          755                760                     765

Thr  Leu  Asn  Thr  Leu  Trp  Ile  Asn  Gly  Gln  Lys  Ile  Glu  Asn  Met  Pro
     770                775                     780

Tyr  Gln  Thr  Thr  Leu  Gln  Gln  Gly  Asp  Trp  Leu  Ile  Asp  Ser  Asn  Gly
785                      790                795                           800

Asn  Gly  Tyr  Leu  Ile  Thr  Gln  Ala  Glu  Lys  Val  Asn  Val  Ser  Arg  Gln
               805                810                          815

His  Gln  Val  Ser  Ala  Glu  Asn  Lys  Asn  Arg  Gln  Pro  Thr  Glu  Gly  Asn
               820                825                     830

Phe  Ser  Ser  Ala  Trp  Ile  Asp  His  Ser  Thr  Arg  Pro  Lys  Asp  Ala  Ser
          835                840                     845

Tyr  Glu  Tyr  Met  Val  Phe  Leu  Asp  Ala  Thr  Pro  Glu  Lys  Met  Gly  Glu
     850                855                     860

Met  Ala  Gln  Lys  Phe  Arg  Glu  Asn  Asn  Gly  Leu  Tyr  Gln  Val  Leu  Arg
865                      870                875                           880

Lys  Asp  Lys  Asp  Val  His  Ile  Ile  Leu  Asp  Lys  Leu  Ser  Asn  Val  Thr
                    885                890                          895

Gly  Tyr  Ala  Phe  Tyr  Gln  Pro  Ala  Ser  Ile  Glu  Asp  Lys  Trp  Ile  Lys
               900                905                          910

Lys  Val  Asn  Lys  Pro  Ala  Ile  Val  Met  Thr  His  Arg  Gln  Lys  Asp  Thr
          915                920                     925

Leu  Ile  Val  Ser  Ala  Val  Thr  Pro  Asp  Leu  Asn  Met  Thr  Arg  Gln  Lys
     930                935                     940

Ala  Ala  Thr  Pro  Val  Thr  Ile  Asn  Val  Thr  Ile  Asn  Gly  Lys  Trp  Gln
945                      950                955                           960

Ser  Ala  Asp  Lys  Asn  Ser  Glu  Val  Lys  Tyr  Gln  Val  Ser  Gly  Asp  Asn
               965                970                          975

Thr  Glu  Leu  Thr  Phe  Thr  Ser  Tyr  Phe  Gly  Ile  Pro  Gln  Glu  Ile  Lys
     980                985                     990

Leu  Ser  Pro  Leu  Pro
          995
```

(2) INFORMATION FOR SEQ ID NO:2:

(i) SEQUENCE CHARACTERISTICS:
        (A) LENGTH: 990 amino acids
        (B) TYPE: amino acid
        (D) TOPOLOGY: linear (ii) MOLECULE TYPE: protein (xi) SEQUENCE DESCRIPTION: SEQ ID NO:2:

```
Leu  Pro  Thr  Leu  Ser  His  Glu  Ala  Phe  Gly  Asp  Ile  Tyr  Leu  Phe  Glu
 1             5                   10                          15

Gly  Glu  Leu  Pro  Asn  Thr  Leu  Thr  Thr  Ser  Asn  Asn  Asn  Gln  Leu  Ser
```

-continued

|  |  |  |  | 20 |  |  |  |  | 25 |  |  |  |  | 30 |  |
|---|---|---|---|---|---|---|---|---|---|---|---|---|---|---|---|
| Leu | Ser | Lys 35 | Gln | His | Ala | Lys | Asp 40 | Gly | Glu | Gln | Ser | Leu 45 | Lys | Trp | Gln |
| Tyr | Gln 50 | Pro | Gln | Ala | Thr | Leu 55 | Thr | Leu | Asn | Asn | Ile 60 | Val | Asn | Tyr | Gln |
| Asp 65 | Asp | Lys | Asn | Thr | Ala 70 | Thr | Pro | Leu | Thr | Phe 75 | Met | Met | Trp | Ile | Tyr 80 |
| Asn | Glu | Lys | Pro | Gln 85 | Ser | Ser | Pro | Leu | Thr 90 | Leu | Ala | Phe | Lys | Gln 95 | Asn |
| Asn | Lys | Ile | Ala 100 | Leu | Ser | Phe | Asn | Ala 105 | Glu | Leu | Asn | Phe | Thr 110 | Gly | Trp |
| Arg | Gly | Ile 115 | Ala | Val | Pro | Phe | Arg 120 | Asp | Met | Gln | Gly | Ser 125 | Ala | Thr | Gly |
| Gln | Leu 130 | Asp | Gln | Leu | Val | Ile 135 | Thr | Ala | Pro | Asn | Gln 140 | Ala | Gly | Thr | Leu |
| Phe 145 | Phe | Asp | Gln | Ile | Ile 150 | Met | Ser | Val | Pro | Leu 155 | Asp | Asn | Arg | Trp | Ala 160 |
| Val | Pro | Asp | Tyr | Gln 165 | Thr | Pro | Tyr | Val | Asn 170 | Asn | Ala | Val | Asn | Thr 175 | Met |
| Val | Ser | Lys | Asn 180 | Trp | Ser | Ala | Leu | Leu 185 | Met | Tyr | Asp | Gln | Met 190 | Phe | Gln |
| Ala | His | Tyr 195 | Pro | Thr | Leu | Asn | Phe 200 | Asp | Thr | Glu | Phe | Arg 205 | Asp | Asp | Gln |
| Thr | Glu 210 | Met | Ala | Ser | Ile | Tyr 215 | Gln | Arg | Phe | Glu | Tyr 220 | Tyr | Gln | Gly | Ile |
| Arg 225 | Ser | Asp | Lys | Lys | Ile 230 | Thr | Pro | Asp | Met | Leu 235 | Asp | Lys | His | Leu | Ala 240 |
| Leu | Trp | Glu | Lys | Leu 245 | Val | Leu | Thr | Gln | His 250 | Ala | Asp | Gly | Ser | Ile 255 | Thr |
| Gly | Lys | Ala | Leu 260 | Asp | His | Pro | Asn | Arg 265 | Gln | His | Phe | Met | Lys 270 | Val | Glu |
| Gly | Val | Phe 275 | Ser | Glu | Gly | Thr | Gln 280 | Lys | Ala | Leu | Leu | Asp 285 | Ala | Asn | Met |
| Leu | Arg 290 | Asp | Val | Gly | Lys | Thr 295 | Leu | Leu | Gln | Thr | Ala 300 | Ile | Tyr | Leu | Arg |
| Ser 305 | Asp | Ser | Leu | Ser | Ala 310 | Thr | Asp | Arg | Lys | Lys 315 | Leu | Glu | Glu | Arg | Tyr 320 |
| Leu | Leu | Gly | Thr | Arg 325 | Tyr | Val | Leu | Glu | Gln 330 | Gly | Phe | Thr | Arg | Gly 335 | Ser |
| Gly | Tyr | Gln | Ile 340 | Ile | Thr | His | Val | Gly 345 | Tyr | Gln | Thr | Arg | Glu 350 | Leu | Phe |
| Asp | Ala | Trp 355 | Phe | Ile | Gly | Arg | His 360 | Val | Leu | Ala | Lys | Asn 365 | Asn | Leu | Leu |
| Ala | Pro 370 | Thr | Gln | Gln | Ala | Met 375 | Met | Trp | Tyr | Asn | Ala 380 | Thr | Gly | Arg | Ile |
| Phe 385 | Glu | Lys | Asn | Asn | Glu 390 | Ile | Val | Asp | Ala | Asn 395 | Val | Asp | Ile | Leu | Asn 400 |
| Thr | Gln | Leu | Gln | Trp 405 | Met | Ile | Lys | Ser | Leu 410 | Leu | Met | Leu | Pro | Asp 415 | Tyr |
| Gln | Gln | Arg | Gln 420 | Gln | Ala | Leu | Ala | Gln 425 | Leu | Gln | Ser | Trp | Leu 430 | Asn | Lys |
| Thr | Ile | Leu 435 | Ser | Ser | Lys | Gly | Val 440 | Ala | Gly | Gly | Phe | Lys 445 | Ser | Asp | Gly |

```
Ser  Ile  Phe  His  His  Ser  Gln  His  Tyr  Pro  Ala  Tyr  Ala  Lys  Asp  Ala
     450                 455                      460

Phe  Gly  Gly  Leu  Ala  Pro  Ser  Val  Tyr  Ala  Leu  Ser  Asp  Ser  Pro  Phe
465                      470                      475                      480

Arg  Leu  Ser  Thr  Ser  Ala  His  Glu  Arg  Leu  Lys  Asp  Val  Leu  Leu  Lys
                    485                      490                      495

Met  Arg  Ile  Tyr  Thr  Lys  Glu  Thr  Gln  Ile  Pro  Val  Val  Leu  Ser  Gly
               500                      505                      510

Arg  His  Pro  Thr  Gly  Leu  His  Lys  Ile  Gly  Ile  Ala  Pro  Phe  Lys  Trp
          515                      520                      525

Met  Ala  Leu  Ala  Gly  Thr  Pro  Asp  Gly  Lys  Gln  Lys  Leu  Asp  Thr  Thr
     530                      535                      540

Leu  Ser  Ala  Ala  Tyr  Ala  Lys  Leu  Asp  Asn  Lys  Thr  His  Phe  Glu  Gly
545                      550                      555                      560

Ile  Asn  Ala  Glu  Ser  Glu  Pro  Val  Gly  Ala  Trp  Ala  Met  Asn  Tyr  Ala
               565                      570                      575

Ser  Met  Ala  Ile  Gln  Arg  Arg  Ala  Ser  Thr  Gln  Ser  Pro  Gln  Gln  Ser
               580                      585                      590

Trp  Leu  Ala  Ile  Ala  Arg  Gly  Phe  Ser  Arg  Tyr  Leu  Val  Gly  Asn  Glu
          595                      600                      605

Ser  Tyr  Glu  Asn  Asn  Asn  Arg  Tyr  Gly  Arg  Tyr  Leu  Gln  Tyr  Gly  Gln
     610                      615                      620

Leu  Glu  Ile  Ile  Pro  Ala  Asp  Leu  Thr  Gln  Ser  Gly  Phe  Ser  His  Ala
625                      630                      635                      640

Gly  Trp  Asp  Trp  Asn  Arg  Tyr  Pro  Gly  Thr  Thr  Ile  His  Leu  Pro
                    645                      650                      655

Tyr  Asn  Glu  Leu  Glu  Ala  Lys  Leu  Asn  Gln  Leu  Pro  Ala  Ala  Gly  Ile
               660                      665                      670

Glu  Glu  Met  Leu  Leu  Ser  Thr  Glu  Ser  Tyr  Ser  Gly  Ala  Asn  Thr  Leu
          675                      680                      685

Asn  Asn  Asn  Ser  Met  Phe  Ala  Met  Lys  Leu  His  Gly  His  Ser  Lys  Tyr
     690                      695                      700

Gln  Gln  Gln  Ser  Leu  Arg  Ala  Asn  Lys  Ser  Tyr  Phe  Leu  Phe  Asp  Asn
705                      710                      715                      720

Arg  Val  Ile  Ala  Leu  Gly  Ser  Gly  Ile  Glu  Asn  Asp  Lys  Gln  His
                    725                      730                      735

Thr  Thr  Glu  Thr  Thr  Leu  Phe  Gln  Phe  Ala  Val  Pro  Lys  Leu  Gln  Ser
               740                      745                      750

Val  Ile  Ile  Asn  Gly  Lys  Lys  Val  Asn  Gln  Leu  Asp  Thr  Gln  Leu  Thr
          755                      760                      765

Leu  Asn  Asn  Ala  Asp  Thr  Leu  Ile  Asp  Pro  Ala  Gly  Asn  Leu  Tyr  Lys
     770                      775                      780

Leu  Thr  Lys  Gly  Gln  Thr  Val  Lys  Phe  Ser  Tyr  Gln  Lys  Gln  His  Ser
785                      790                      795                      800

Leu  Asp  Asp  Arg  Asn  Ser  Lys  Pro  Thr  Glu  Gln  Leu  Phe  Ala  Thr  Ala
               805                      810                      815

Val  Ile  Ser  His  Gly  Lys  Ala  Pro  Ser  Asn  Glu  Asn  Tyr  Glu  Tyr  Ala
          820                      825                      830

Ile  Ala  Ile  Glu  Ala  Gln  Asn  Asn  Lys  Ala  Pro  Glu  Tyr  Thr  Val  Leu
     835                      840                      845

Gln  His  Asn  Asp  Gln  Leu  His  Ala  Val  Lys  Asp  Lys  Ile  Thr  Gln  Glu
850                      855                      860

Glu  Gly  Tyr  Ala  Phe  Phe  Glu  Ala  Thr  Lys  Leu  Lys  Ser  Ala  Asp  Ala
865                      870                      875                      880
```

| | | | | | | | | | | | | | | |
|---|---|---|---|---|---|---|---|---|---|---|---|---|---|---|
| Thr | Leu | Leu | Ser | Ser 885 | Asp | Ala | Pro | Val 890 | Val | Met | Ala | Lys | Ile 895 | Gln |
| Asn | Gln | Gln | Leu 900 | Thr | Leu | Ser | Ile | Val 905 | Asn | Pro | Asp | Leu | Asn 910 | Leu | Tyr |
| Gln | Gly | Arg 915 | Glu | Lys | Asp | Gln | Phe 920 | Asp | Asp | Lys | Gly | Asn 925 | Gln | Ile | Glu |
| Val | Ser 930 | Val | Tyr | Ser | Arg | His 935 | Trp | Leu | Thr | Ala | Glu 940 | Ser | Gln | Ser | Thr |
| Asn 945 | Ser | Thr | Ile | Thr | Val 950 | Lys | Gly | Ile | Trp | Lys 955 | Leu | Thr | Thr | Pro | Gln 960 |
| Pro | Gly | Val | Ile | Ile 965 | Lys | His | His | Asn | Asn 970 | Asn | Thr | Leu | Ile | Thr 975 | Thr |
| Thr | Thr | Ile | Gln 980 | Ala | Thr | Pro | Thr | Val 985 | Ile | Asn | Leu | Val | Lys 990 | | |

+

PROTEIN VULGARIS CHONDROITINASE II

This application is a continuation-in-part of:

(A) U.S. Ser. No. 08/231,534, filed Apr. 22, 1994, now U.S. Pat. No. 5,525,500; and (B) U.S. Ser. No. 08/232,540, filed Apr. 22, 1994, now U.S. Pat. No. 5,498,536.

FIELD OF THE INVENTION

This invention relates to the identification, isolation, and purification of the enzyme chondroitinase II and to the copurification of the enzymes chondroitinase I and chondroitinase II. Compositions of the copurified enzyme mixture or a combination of the isolated individual enzymes are useful for selectively and completely disinserting the ocular vitreous body from the neural retina of the eye.

BACKGROUND OF THE INVENTION

Chondroitinases are enzymes of bacterial origin that act on chondroitin sulfate, a component of the proteoglycans that mediate the attachment between the retina and the vitreous body of the human eye. Examples of chondroitinase enzymes are chondroitinase ABC which is produced by the bacterium *Proteus vulgaris* (*P. vulgaris*), and chondroitinase AC, which is produced by *A. aurescens*. Chondroitinase ABC is designated as chondroitinase I in the present invention. Chondroitinases ABC and AC function by degrading polysaccharide side chains in protein-polysaccharide complexes, without degrading the protein core.

When resolved by SDS-PAGE, chondroitinase I migrates with an apparent molecular mass of about 110 kDa (see FIG. 1). Others have reported the appearance of a doublet in SDS-PAGE resolution of chondroitinase I (Sato et al., *Agric. Biol. Chem.* 50:4,1057–1059 (1986)). The present inventors have discovered that this doublet represents intact chondroitinase I and 90 a kDa degradation product. Commercial chondroitinase I protein preparations contain variable amounts of 90 kDa protein and 18 kDa protein degradation product fragments (see FIG. 1).

Yamagata et al. (*J. Biol. Chem.* 243:1523–1535 (1968)) describe the purification of the chondroitinase ABC from extracts of *P. vulgaris*. This enzyme selectively degrades the glycosaminoglycans chondroitin-4-sulfate, dermatan sulfate and chondroitin-6-sulfate (also referred to respectively as chondroitin sulfates A, B, and C which are side chains of proteoglycans) at pH 8 at higher rates than chondroitin or hyaluronic acid. The products of the degradation are large molecular weight unsaturated oligosaccharides and an unsaturated disaccharide. However, chondroitinase ABC does not attack keratosulfate, heparin or heparitin sulfate.

Kikuchi et al., U.S. Pat. No. 5,198,355, describe the purification of glycosaminoglycan degrading enzymes, such as chondroitinase ABC, by fractionating the enzyme by adsorbing a solution containing the enzyme onto an insoluble sulfated polysaccharide carrier and then desorbing the individual enzyme from the carrier.

The chondroitinase enzymes have use in ocular surgery as a means for rapid and specific non-surgical disruption of the attachment of the vitreous body to the neural retina of the eye, thereby facilitating removal of the vitreous body. For example, Hageman, U.S. Pat. No. 5,292,509, describes an ophthalmic vitrectomy method for selectively and completely disinserting (removing) the ocular vitreous body, epiretinal membranes, or fibrocellular membranes from the neural retina, ciliary epithelium and posterior lens surface of the mammalian eye as an adjunct to vitrectomy. An effective amount of an enzyme which disrupts or degrades chondroitin sulfate proteoglycan localized specifically to sites of vitreoretinal adhesion is administered to the eye thereby permitting complete disinsertion of the vitreous body and/or epiretinal membranes. The enzyme can be a protease-free glycosaminoglycanase. Hageman utilized chondroitinase ABC obtained from Seikagaku Koryo Co., Ltd., Tokyo, Japan, an impure preparation that typically includes chondroitinase I degradation products and/or proteinaceous stabilizers. Proteinaceous stabilizers are undesirable because they are unacceptable in therapeutic or surgical compositions to be administered to the human eye.

Some chondroitinases have also been described as having value in dissolving the cartilage of herniated discs without disturbing the stabilizing collagen components of discs.

Brown, U.S. Pat. No. 4,696,816, describes a method for treating intervertebral disc displacement in mammals, including humans, by injecting into the intervertebral disc space effective amounts of a solution containing chondroitinase ABC. The chondroitinase ABC was isolated and purified from extracts of *P. vulgaris*. This native enzyme material functioned to dissolve cartilage, such as herniated spinal discs. Specifically, the enzyme causes the selective chemonucleolysis of the nucleus pulposus which contains proteoglycans and randomly dispersed collagen fibers.

Another chondroitinase, chondroitinase II, has now been isolated and purified from *P. vulgaris* by the present inventors. Additionally, the present inventors have discovered an efficient copurification method in which a mixture chondroitinase I and chondroitinase II can be conveniently obtained.

BRIEF DESCRIPTION OF THE DRAWINGS

FIG. 10 is a graphic illustration of the co-purification of chondroitinases I and II by MacroPrep High Q anion exchange chromatography. The inset is an illustration of an SDS-PAGE (4–20%) of:

Figure 1:
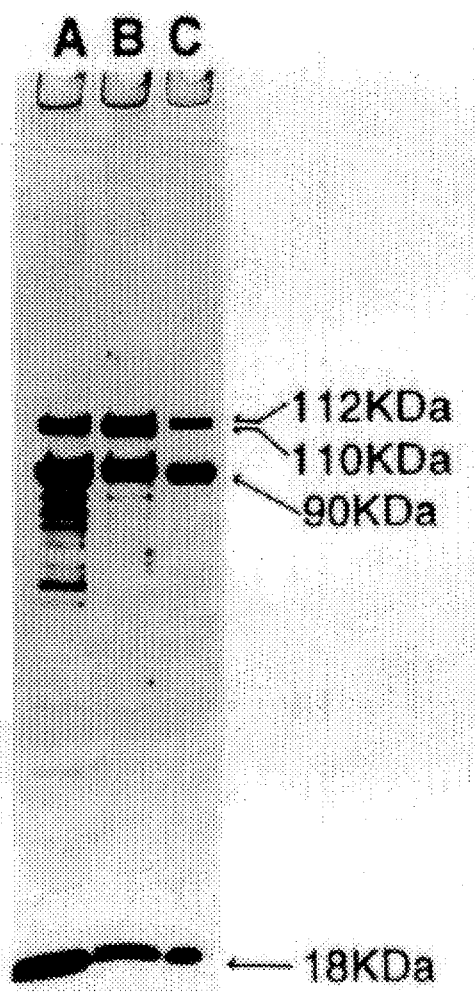
FIG. 1 is an illustration of an SDS-PAGE gel of the antibody affinity chromatographic fractionation of a chondroitinase enzyme preparation. Lane A is the unfractionated chondroitinase and Lanes B and C are affinity purified chondroitinases I (110 kDa) and II (112 kDa) and one of the degradation products of chondroitinase I (90 kDa).

Lane 1—Load of High Q, diluted 5 fold;
Lanes 2, 3—Flow through of High Q, diluted 5 fold;
Lanes 4, 5—Flow through of High Q, diluted 10 fold;
Lanes 6, 7—Flow through of High Q, diluted 20 fold;
Lanes 8, 9—Flow through of High Q, diluted 40 fold;
Lane 10—Flow through of High Q, diluted 80 fold;
Lane 11—Standard Chondroitinase.

Figure 11:
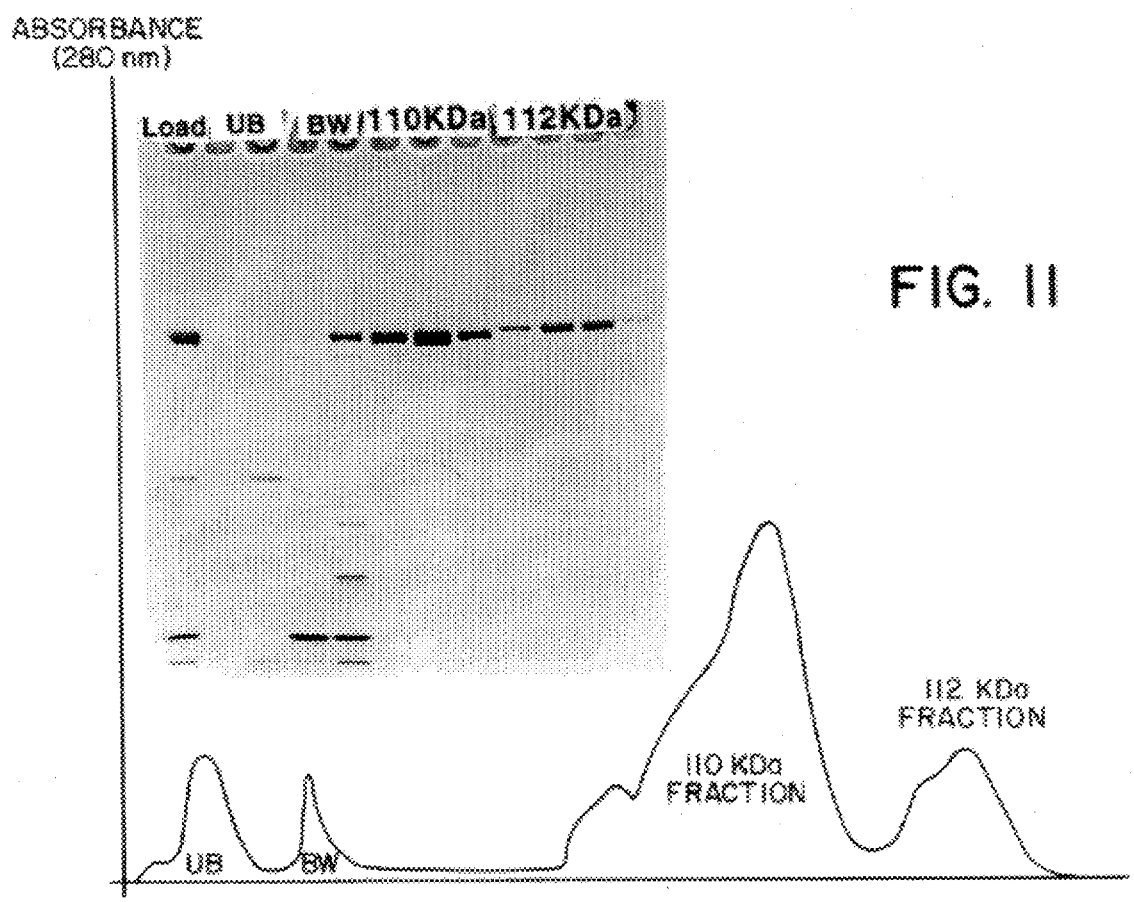

FIG. 11 is an illustration of the individual separation of chondroitinases I and II using MacroPrep High S cation exchange chromatography. The graph shows the absorbance at 280 nm of the column eluate. The inset is an illustration of the SDS-PAGE profiles of the material loaded on the column (LOAD); the unbound material (UB); the buffer wash (BW); chondroitinase I (110 kDa); and chondroitinase II (112 kDa).

SUMMARY OF THE INVENTION

Chondroitinase II, a protein having an isoelectric point of approximately 8.4–8.45 and an apparent molecular mass of 112 kDa when electrophoresed in a 4 to 20% gradient acrylamide gel in 25 mM Tris/192 mM glycine buffer at pH 8.5 in the presence of about 0.1% (w/v) SDS, has been isolated and purified. The amino acid sequence of chondroitinase II is provided as SEQ ID NO:2.

A process for the copurification by affinity chromatography of the chondroitinase I and chondroitinase II proteins produced by *Proteus vulgaris* is also provided. The process includes:

(a) preparing a clarified homogenate of induced *P. vulgaris*, the homogenate having a pH of 5.8 to 7.4;

(b) loading the homogenate onto a negatively charged cation exchange resin chromatographic support so that any positively charged proteins comprising chondroitinase I and chondroitinase II in the homogenate form a non-covalent bond with the negatively charged support;

(c) affinity-eluting, in pools, the chondroitinase proteins from the support with an aqueous solution of chondroitin sulfate at a pH 7.0–9.5;

(d) loading the affinity eluted protein pools onto an anion exchange resin chromatographic support to yield an unbound eluate; and (e) recovering the chondroitinase I and chondroitinase II proteins in the unbound eluate.

In another aspect, the proteins can be further purified by metal chelating chromatography. The copurification process typically results in a weight/weight ratio of approximately 60% chondroitinase I:40% chondroitinase II, although ratios of up to approximately 80% chondroitinase I:20% chondroitinase II are also obtained.

Therapeutic or surgical compositions of isolated chondroitinases I and II or the copurified mixture of chondroitinase I and II are also disclosed. Preferably, the amount of chondroitinases I and II is a disinsertion effective amount. These compositions are used in a method for selectively and completely disinserting the vitreous body from the neural retina of an eye. The compositions are administered to an eye in need of such treatment, preferably by intravitreal, subvitreal, sublenticular, and posterior chamber administration.

DETAILED DESCRIPTION OF THE INVENTION

The present invention encompasses the identification and isolation of the enzyme chondroitinase II. Chondroitinase II can be purified separately from the enzyme chondroitinase I, or the two enzymes can be copurified by methods also encompassed by the present invention. These two enzymes are formulated in a composition, preferably in the absence of proteinaceous stabilizers such as, for example, bovine serum albumin, and other impurities that affect the properties of the mixture of these two distinct enzymes. Proteinaceous stabilizers are unsuitable for use in therapeutic or surgical compositions for administration to humans and particularly to the human eye. An assay for chondroitinase II is also provided. Chondroitinases I and II are used together to effect selective and complete disinsertion of the vitreous body from the neural retina of the eye.

Chondroitinase II

Chondroitinase II is an enzyme that is distinct from chondroitinase I, although the two enzymes compliment each other in that each is involved in the complete degradation of proteoglycans involved in vitreoretinal adhesion. When chondroitinase I is resolved by SDS-PAGE, it migrates with an apparent molecular mass of about 110 kDa (FIG. 1). However, chondroitinase I may appear as a doublet because proteolytic degradation products of chondroitinase I may be detected as well. The present inventors have further identified these degradation products, through the use of specific antibodies, as equimolar amounts of 90 kDa and 18 kDA species. FIG. 1 illustrates an SDS-PAGE of the fractionation of an efficacious preparation of chondroitinase by antibody affinity chromatography. The fractionation was conducted as follows:

A fragment of chondroitinase (18 kD) was purified from the (90+18) kD chondroitinase by G.P.C. in 4M urea, free of the contaminating proteins (which have much higher molecular weights.) Antibodies were produced against the 18 kDa fragment. A chondroitinase affinity gel was prepared to covalently attach amino groups of recombinant chondroitinase to the gel. Purified 18 kDa specific IgG from serum were prepared using the affinity column. The 18 kDa specific was covalently coupled on a protein A-Gel. Protein A binds the constant region of IgG and hence properly orients the binding region. The minor components from chondroitinase were fractionated using gel. Both species of degradation product are presumably formed by at least one endoproteolytic cleavage within the intact chondroitinase I protein likely resulting from impurities in typical chondroitinase I preparations.

Isolated, purified chondroitinase II protein was analyzed for its physical and chemical properties.

SDS-PAGE and Mass Spectrometry

Chondroitinase II migrates under certain SDS-PAGE conditions more slowly than the intact chondroitinase I protein. Chondroitinase II could not be detected in conventional SDS-PAGE systems, however. It was isolated and identified by the present inventors from a gradient of acrylamide in 23 mM Tris/192 mM glycine buffer at pH 8.5 in the presence of about 0.1% (w/v) SDS. A 7% gel can also be use.

Figure 2:
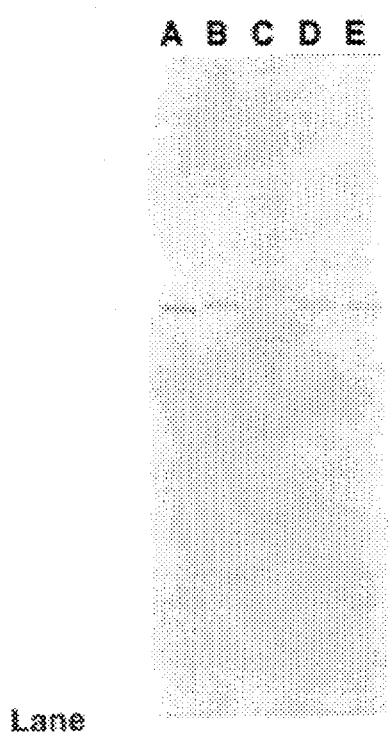
FIG. 2 is an illustration of an SDS-PAGE gel of a preparation of chondroitinase enzymes preparation. Lane A is the purified chondroitinase I protein; Lane B is the purified chondroitinase II protein; Lane C is a 90 kilodalton enzymatic cleavage or degradation product of chondroitinase I protein; Lane D is the chondroitinase enzyme preparation with a doublet composed of the chondroitinase I and chondroitinase II proteins.

Chondroitinase II has an apparent molecular mass of 112 kDa when electrophoresed by SDS-PAGE as described above. It is observed as the upper band of the previously unresolved doublet of FIG. 2, lane D.

The mass for the purified native chondroitinase II found by mass spectrometry is $111,772\pm27$ daltons by electrospray and $111,725\pm20$ daltons by laser desorption. These data correspond to the mass predicted from the DNA sequence that encodes chondroitinase II and to the mass found for recombinant chondroitinase II. The mass for chondroitinase II is 700–800 daltons less than that for chondroitinase I, even though in an SDS-PAGE gel the chondroitinase II band is the upper band of the doublet.

Isoelectric Point

Isoelectric focusing (IEF) of the chondroitinase II protein yields an isoelectric point (pI) of approximately 8.4–8.45, which is similar to that for the two isoforms of chondroitinase I, which have pIs of approximately 8.3–8.35 and 8.4–8.45, respectively. (See FIG. 3). IEF conditions were as follows:

The ampholine range used was pH 8 to 9.5 in a 5% polyacrylamide gel. The pH gradient was induced by 1M $H_3PO_4$ and 1M NaOH, respectively.

Sequencing

The derived amino acid sequences of chondroitinases I and II are illustrated in SEQ ID NO:1 and SEQ ID NO:2, respectively. Although the two proteins may appear as a single band by standard SDS-PAGE, they resolve as a doublet under the special SDS-PAGE conditions described herein. The distinct nature of these two proteins is further confirmed by sequencing of the first forty amino acid residues at the amino-terminal of each protein as well as from the remainder of their amino acid sequences which were predicted from their nucleotide sequences.

Amino-terminal sequencing of the isolated and purified native chondroitinase II protein confirms that it has the same amino-terminal sequence as that predicted from the nucleotide sequence and determined by amino-terminal sequencing for the recombinantly-produced chondroitinase II protein that was conducted using a ProSequencer Model 6600 (Milligen/Biosearch, Milford, Mass.) and following the manufacturer's instruction manual.

In particular, the first twenty residues (SEQ ID NO:2) of the amino-terminus are identical for native and recombinant chondroitinase II except that recombinant chondroitinase II includes an amino terminal methionine residue which is not present in the native protein. Sequencing of residues 21–40 was difficult due to increased non-specific Edman degradation. However, to the extent reliable identification of residues in this region was made, the residues are identical (except as explained above) for the native and recombinant chondroitinase II. The same is true for sequencing of the amino-terminus of the native and recombinant chondroitinase I (SEQ ID NO:1).

Antibody Binding Studies

Further evidence for the distinctiveness of chondroitinase I and chondroitinase II is provided by polyclonal antibody binding studies on Western blots. Chondroitinase I binds as expected to a polyclonal antibody against chondroitinase I, but does not bind (cross-react) to a polyclonal antibody against chondroitinase II. Similarly, chondroitinase II binds as expected to a polyclonal antibody against chondroitinase II, but does not bind (cross-react) to a polyclonal antibody against chondroitinase I.

Additionally, two different behaviors are observed under native and denaturing conditions as well. Under denaturing conditions, such as detergent treatment with SDS, there is no cross-reaction between the two chondroitinase proteins. This indicates that there are no shared (sequence-dependent) epitopes when the molecules are unfolded. Under non-denaturing conditions (native), there is evidence that at least one epitope is shared, based on antibody affinity chromatography results, where there is copurification. Without being bound by any theory, it is believed that this epitope could be located at the chondroitin sulfate binding/recognition site of these proteins. This region may exhibit a conserved three dimensional arrangement of amino acids which bind the chondroitin sulfate substrate. Conformational epitopes, unlike sequence-dependent epitopes, are lost when the proteins are denatured. Thus, the antibody binds only to the native, but not to the denatured proteins.

The chondroitinase II protein also has high affinity to heparin sulfate, as does chondroitinase I.

Biological Activity

The biological activity of the chondroitinase II protein is also different than that of chondroitinase I. Chondroitinase II biological activity was first examined by selectively removing the chondroitinase II protein from a batch of chondroitinase enzyme preparation that had been shown previously to be active in vivo. When this batch lacking chondroitinase II was tested, it was no longer fully effective in vivo and resulted in an incomplete vitreous disinsertion.

The action of chondroitinase I and chondroitinase II upon proteoglycan was further tested in vitro using thin layer chromatography. As will be described in detail below, chondroitinase I by random endolytic cleavage generates a mixture of sugars in the initial stages. Extensive digestion by chondroitinase I generates three end products, one of which one is the end product disaccharides (mainly the 6S form). However, two additional digestion products are seen, one migrating at about one-third and the other migrating at about two-thirds the R.F. seen for the disaccharides.

In contrast, chondroitinase II by itself does not digest proteoglycan. However, when chondroitinase II is added to chondroitinase I, neither of the two additional digestion products are seen; instead, all the material is digested to completion, that is, to the disaccharides. These results are replicated when chondroitin sulfate is substituted for proteoglycan. This complete digestion is seen even at low proportions of chondroitinase II. A 90% chondroitinase I:10% chondroitinase II (w/w) mixture provides complete digestion of the proteoglycan or chondroitin sulfate to disaccharides. These results were also replicated in the in vivo experiments described below.

In the eye, the chondroitinase proteins degrade the chondroitin sulfate side chains of proteoglycan, but not the protein core of proteoglycan. Therefore, for in vitro studies, it is acceptable to use chondroitin sulfate instead of proteoglycan, because chondroitin sulfate is the moiety attacked by the proteins and because the cost of obtaining chondroitin sulfate is much lower than proteoglycan.

The nature of the products of the degradation of chondroitin sulfate by the chondroitinase I and chondroitinase II proteins was examined by thin layer chromatography (TLC)

Figure 4:
FIG. 4 is an illustration of an analysis by thin layer chromatography of the digestion of proteoglycan by chondroitinase I and chondroitinase II proteins.

(see FIG. 4), gel permeation chromatography (GPC), and mass spectrometry.

First, a silica gel based TLC method was developed to separate the disaccharide degradation products of chondroitin sulfate and proteoglycan and to identify the unknown sugars. The disaccharides 0S, 4S and 6S were all separated. The solvent system used contained various proportions of ethyl acetate, acetic acid and water. The disaccharides were visualized by alkaline silver nitrate, which stains reducing sugars brown. Because TLC requires only 0.025 ml of sample, it allowed the use of the expensive proteoglycan as a substrate, which was compared to chondroitin sulfate.

Using one dimensional TLC to analyze products, when chondroitinase I acts on proteoglycan, there were two oligosaccharides of unknown composition that were generated besides the disaccharide, which was the major product. These two oligosaccharides migrated at ⅓ and ⅔ the R.F. seen for the disaccharide. The ⅔ R.F. sugar eventually was cleaved by the chondroitinase I, over an extended time period (at a rate at least one hundred times slower than the rate at which chondroitinase II cleaves this sugar). In contrast, the ⅓ R.F. sugar was not cleaved even after an extended incubation. However, if 10% by weight of the chondroitinase I protein was substituted by the chondroitinase II protein, both the ⅔ R.F. and the ⅓ R.F. sugar were rapidly digested, to an extent that they did not accumulate at detectable levels.

The TLC experiment was repeated in two dimensions, first with digestion by chondroitinase I and then with digestion by chondroitinase II. Proteoglycan was digested by chondroitinase I and then chromatographed along the first dimension of a TLC. The separated sugars were then digested with pure chondroitinase II protein on the TLC plate. The plate was then run along the second dimension under the same conditions used for the first dimension. Thus, the sugars that were not cleaved by the chondroitinase II protein migrate along the diagonal, while those that were cleaved had altered migration characteristics of the products causing the products to migrate away from the diagonal.

The results show that all spots except the oligosaccharide migrating at about one-third the R.F. were at the diagonal. This indicates that most sugars generated by digestion of proteoglycan by chondroitinase I were not further digested by the chondroitinase II protein. However, this particular oligosaccharide was completely absent from the diagonal position and instead showed two spots migrating faster, indicating that it was cleaved to two smaller saccharides.

TLC was then repeated using micro-preparative techniques to isolate these unknown sugars, by scraping and extracting them off the TLC plate. These isolated sugars were then analyzed. Ten mg of proteoglycan (ICN Biomedical Costa Mesa, Calif.) were digested with 8 µg of either recombinant or purified native chondroitinase I protein for 1 hour at 37° C., and the products were chromatographed on TLC plates, loading the samples as streaks. After chromatography, the silica gel was scraped from the TLC plates as bands 5 mm apart. These silica gel pools were extracted three times using deionized water, which was expected to solubilize most of the oligosaccharide present in these fractions. These fractions were then chromatographed on TLC, to identify the fraction containing the oligosaccharide of interest. The fraction containing the disaccharide was also identified and was used as a control in subsequent experiments.

The analysis of saccharide samples (including the ⅓ R.F. sugar) recovered from micro-preparative TLC was not fully successful, probably because of interference from silicates extracted from the TLC plate with the sugars. The low amount of sugars recovered by this method also contributed to difficulty of further analyses. To attempt the recovery of digestion products on a larger scale would have been very difficult if proteoglycan were used as substrate, because this material is expensive for small quantities and unavailable commercially in large quantities. As an alternative approach, the abundant and relatively inexpensive substrate chondroitin sulfate was used. This substitute was contaminated with low amounts of intact and partially degraded proteoglycan. In addition, GPC was used for isolation of the sugars.

GPC provided good separation of the sugars, which were recovered in quantities suitable for analysis. In addition, silicate contamination was eliminated (unlike micro-preparative TLC). A recombinantly-expressed chondroitinase I protein was used to obtain the digest. This digest was next chromatographed using GPC. With the two native chondroitinase proteins, even using the purification method described above, trace amounts (less than 1%) of each protein were found in the other; this affected the results by decreasing the yields of the desired tetrasaccharide. It is understood that, in vivo, this is not a concern. Therefore, the native purified chondroitinase proteins are suitable for causing complete vitreal disinsertion in the eye. It is only in the in vitro studies that it is preferred to use recombinant chondroitinase I with the native chondroitinase II. Recombinant chondroitinase I was obtained by the expression in *E. coli* of the gene encoding chondroitinase I through the use of samples deposited with the American Type Culture Collection (ATCC 69234).

Figure 5:
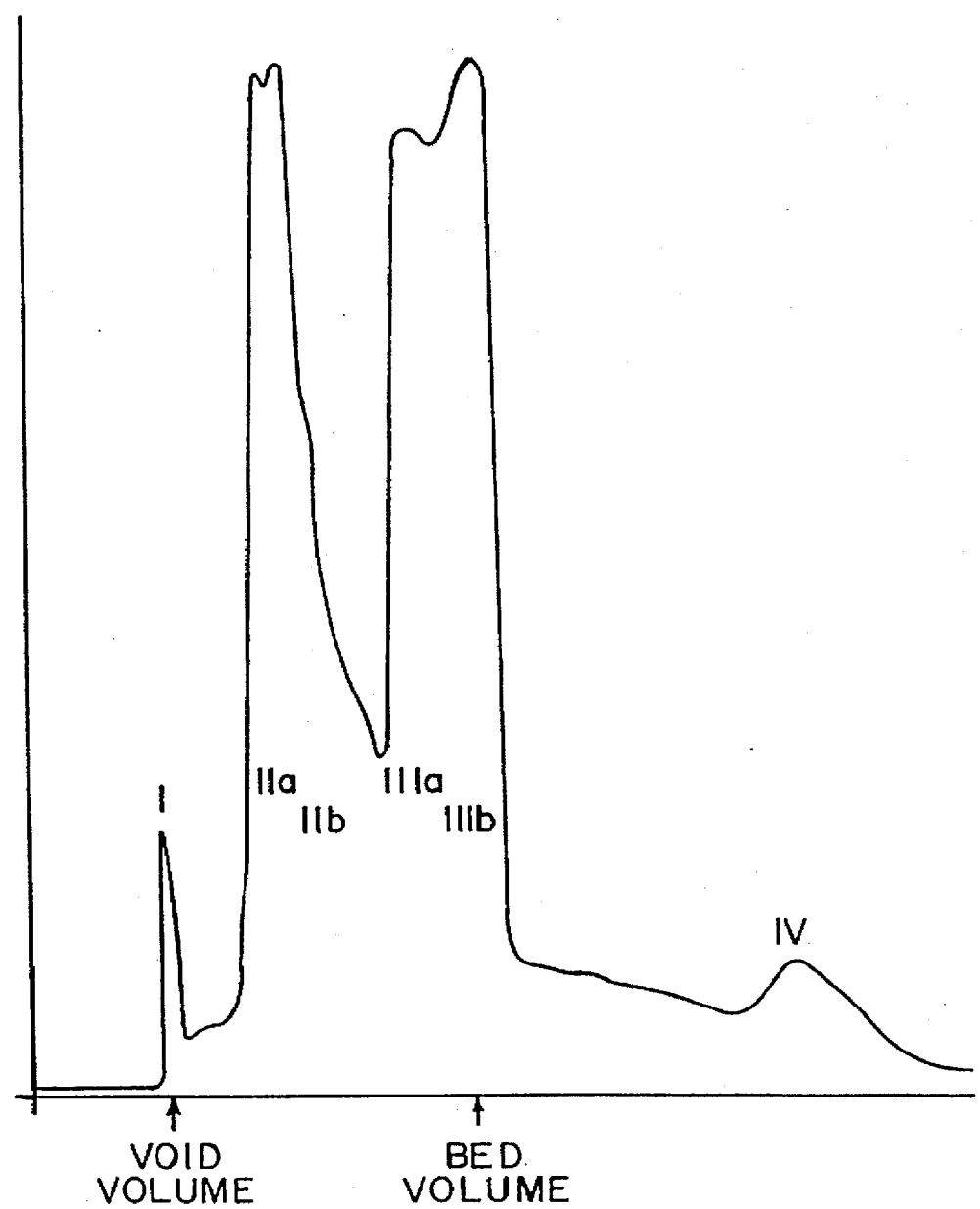
FIG. 5 is an illustration of the component peaks of the digestion of chondroitin sulfate by chondroitinase I, as identified by gel permeation chromatography (GPC). Peak I, eluting at the void volume, is chondroitinase I. Peak II comprises two distinct components designated IIa and IIb, where IIa contains the ⅓ R.F. sugar in an enriched form, while IIb is an oversulfated disaccharide. Peak III (labelled as IIIa and IIIb) elutes close to the bed volume and consists of almost pure disaccharide. Peak IV consists of non-sugar components.

The recombinant chondroitinase I digests chondroitin sulfate into products that were recovered as four peaks from a gel permeation column (Spectra/Gel TAc, Spectrum Medical Industries Inc., Los Angeles, Calif.) run with 0.1% trifluoroacetic acid (TFA) as solvent. The first peak, designated I, was a small peak eluting at the void volume and did not contain any reducing sugar. It was mainly chondroitinase I. The second peak, designated II, comprised two distinct components designated IIa and IIb. IIa contained the ⅓ R.F. sugar in an enriched form, while IIb turned out to be an oversulfated disaccharide. The third peak, designated III, which was the largest, eluted close to the bed volume and consisted of almost pure disaccharide. This GPC is depicted in FIG. 5 (peak III is labelled IIIa and IIIb). Peak IV consists of non-sugar components. (When this procedure was repeated on a GPC-HPLC system with small amounts of proteoglycan instead of chondroitin sulfate, similar results were obtained).

Figure 6:
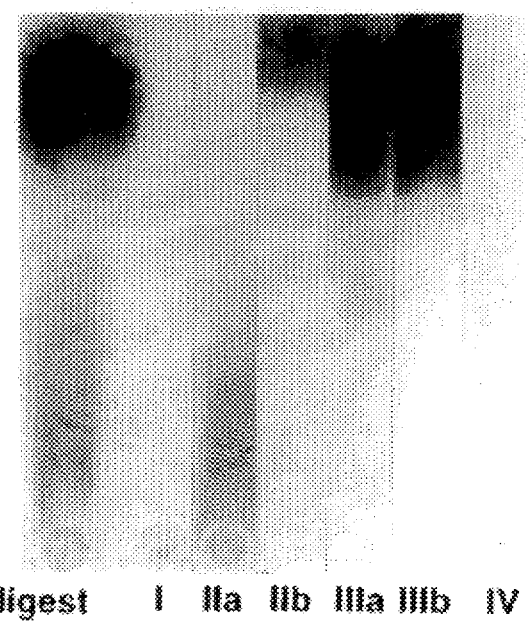
FIG. 6 is an illustration of the analysis by thin layer chromatography (TLC) of the component peaks depicted in FIG. 5. The Lane marked "Digest" is the chondroitin sulfate material that is loaded on the GPC column as digested with chondroitinase I, prior to fractionation by GPC. The other Lanes correspond to the GPC peaks as described for FIG. 5.

The peaks from the GPC of FIG. 5 were analyzed by TLC and the oligosaccharide of interest (Peak IIa) was found to elute with the solvent system described above, free of the major component of the digest, the disaccharides. The fractions were lyophilized to remove the TFA/water and were analyzed. Approximately one-fourth of the digested material was composed of the oligosaccharide, which was obtained as a white crystalline salt-free powder. The results of the TLC are shown in FIG. 6.

The purified oligosaccharide was incubated with different chondroitinase protein preparations, all of them being at a substrate:protein ratio of 1000:1. The pure chondroitinase II protein rapidly digested the oligosaccharide to products that migrated at the position of the disaccharides. Complete digestion was obtained at the first time point tested (15 minutes). As expected, the native chondroitinase I protein had no effect on this oligosaccharide; no disaccharide was generated even by the last time point tested (4 hours). A co-purified mixture (60:40 w/w) of the chondroitinase I and chondroitinase II proteins also cleaved this oligosaccharide, though not as rapidly as with the pure chondroitinase II protein. Significantly, the rate of cleavage of the oligosaccharide correlated quite well with the chondroitinase II protein content. This observation indicates that the oligosaccharide is useful as a specific substrate to quantitate active chondroitinase II protein, without interference from chondroitinase I.

The oligosaccharide corresponding to peak IIa was analyzed using electrospray mass spectroscopy, generating a spectrum corresponding to a mass of 918 daltons. This observed mass fits very well with the calculated mass of a tetrasaccharide of composition 'A—B—A—B', where the two sugars A and B are D-glucuronic acid and monosulfated N-acetyl D-galactosamine, respectively, which are the repeating units of chondroitin sulfate. There were several smaller peaks besides the 919 dalton (M+H) main peak, which is identified as the singly protonated sugar; their masses in order of intensity along with their tentative identification were:

839 da (M–$SO_3$): the monodesulfated sugar 901 da (M–$H_2O$): the monodehydrated sugar 941 da (M+Na): the mono sodium salt 811 da (M—$SO_3$—$H_2O$), 759 da (M—2$SO_3$), 741 da (M—2$SO_3$—$H_2O$), along with traces of other related peaks which correspond to other combinations. In addition, some minor unidentified peaks were also detected, particularly two peaks at 431 da and 531 da. The latter mass fits quite well with the expected mass of a disulfated disaccharide.

Figure 7:
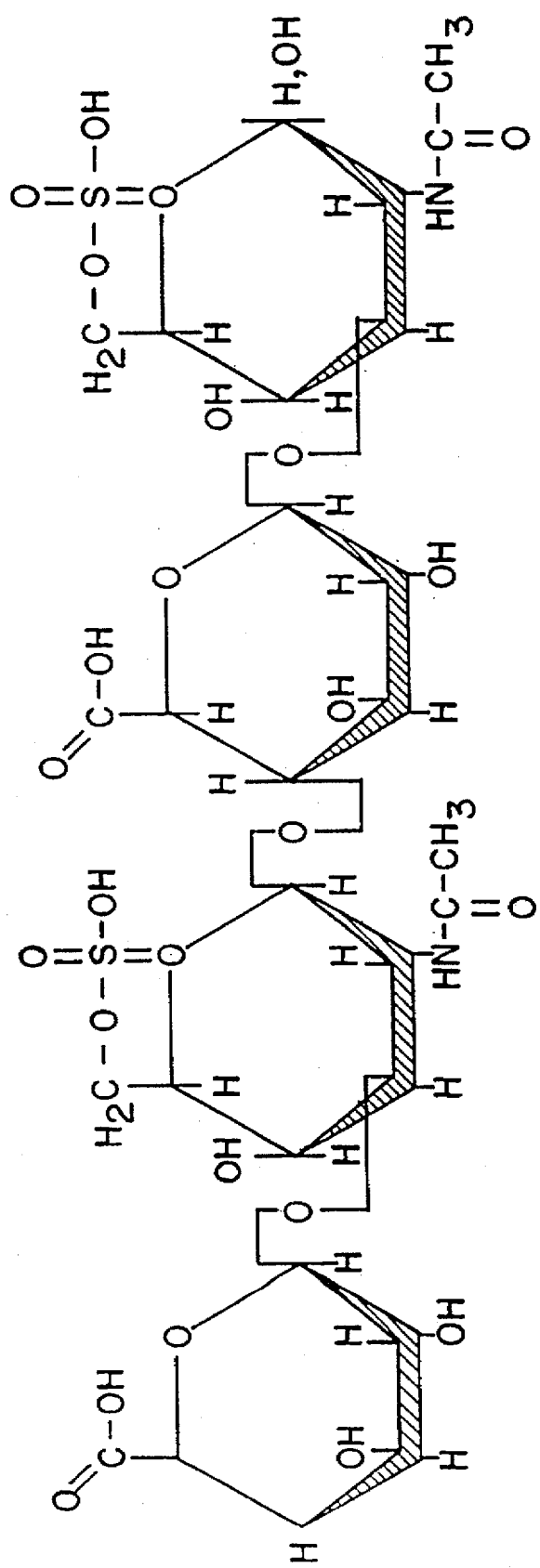
FIG. 7 is an illustration of the 6S form of the tetrasaccharide Δ4,5-D-glucuronic acid-β(1→3)-2N-acetyl, 6-sulfo, D-galactosamine-β(1→4)-D-glucuronic acid-β(1→3)-2N-acetyl, 6-sulfo, D-galactosamine.
Figure 8:
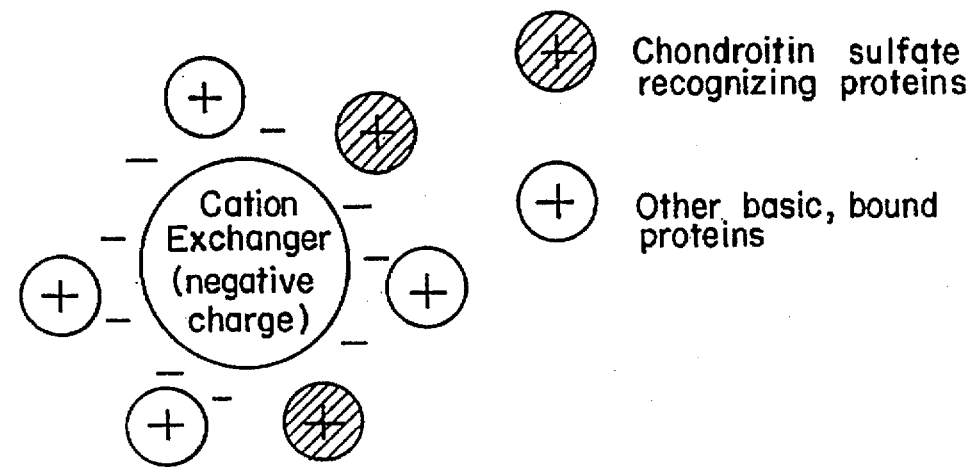
FIG. 8 is a diagrammatic illustration of the preparation and use of the affinity chromatography system of the present invention.
Figure 8:
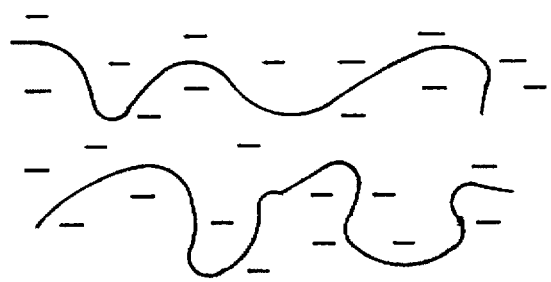
Figure 8:
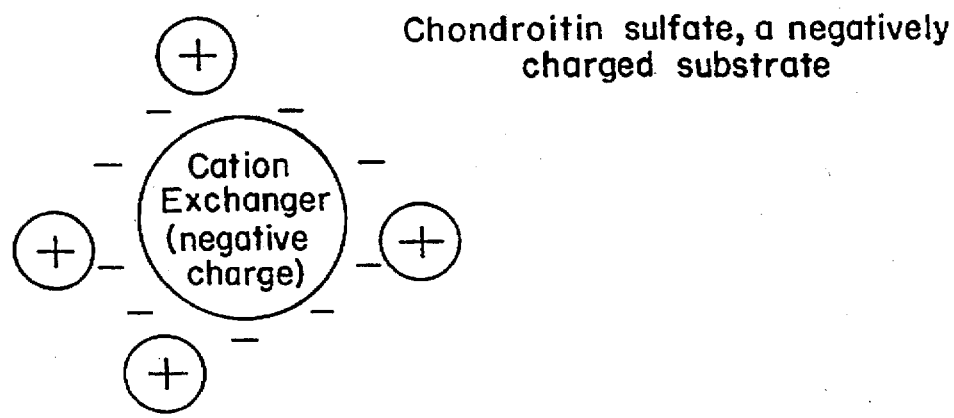
Figure 8:
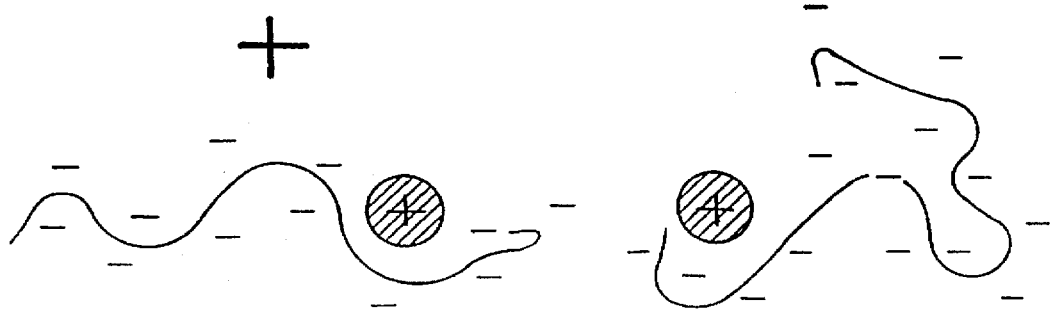

Chondroitinase I partially degrades chondroitin sulfate, yielding an unsaturated disulfated tetrasaccharide with a molecular weight of 918 Daltons as calculated from its chemical formula and as observed by electrospray mass spectrometry. The structure of the major form (about 60%) of the tetrasaccharide is depicted in FIG. 7, where the sulfated side chain is at position 6 of the second and fourth rings from the left. The minor form (about 40%; not depicted) of the tetrasaccharide has this sulfated side chain at position 4 of the second and fourth rings. Both the 4S and 6S sugars are digested at similar rates by chondroitinase II to produce the disaccharides. The tetrasaccharide is referred to as Δ4,5-D-glucuronic acid-β(1→3)-2N-acetyl, 6-sulfo, D-galactosamine-β(1→4)-D-glucuronic acid-β(1→3)-2N-acetyl, 6-sulfo, D-galactosamine (FIG. 7).

Table 1 below compares the characteristics of chondroitinase I and chondroitinase II.

TABLE 1

Comparison of the 110 kDa Chondroitinase I Protein and the 112 kDa Chondroitinase Protein

|  | 110 kDa | 112 kDa |
| --- | --- | --- |
| SDS-PAGE molecular weight | ~110,000 daltons | ~112,000 daltons |
| Electrospray mass spectrometry | 112,527 + 25 daltons | 111,772 + 27 daltons |
| Laser desporption mass spectrometry | 112,508 + 20 daltons | 111,725 + 20 daltons |
| Isoelectric point/s | pH 8.35 and pH 8.45 | pH 8.45 |
| Amino acid composition | absence of cysteines, rich in serine | otherwise similar to 110 kDa |
| Release of di and oligosaccharides from chondroitin sulfate | +++ | — |
| Digestion of oligosaccharides (e.g. Unknown 1, 2) | — | +++ |

Assay

The tetrasaccharide is a good candidate for developing an assay for chondroitinase II, because it is resistant to cleavage by chondroitinase I (a small amount of cleavage of tetrasaccharide to disaccharide by chondroitinase I does occur, but the rate of digestion is several hundred times slower than that seen for chondroitinase II). Conversely, chondroitin sulfate is resistant to cleavage by chondroitinase II. In vitro, the tetrasaccharide is cleaved completely within a few minutes by chondroitinase II, while it is not cleaved over several hours by the same amount of chondroitinase I.

Using the foregoing information, an assay for measuring the activity of the chondroitinase II protein was developed. This assay monitors the conversion of the tetrasaccharide to the disaccharide on high performance liquid chromatography (HPLC). The chondroitinase II protein converts the tetrasaccharide to disaccharides that are separated from the substrate by HPLC on a GPC-HPLC column, such as a Shodex-OH pak KB-802 (Shoko Co. Ltd., Tokyo, Japan), using polymethacrylate as the matrix.

The assay is conducted as follows. First, the tetrasaccharide substrate is prepared in a suitable solution. Pure tetrasaccharide is dissolved in water to an appropriate dilution, such as about 2 mg/ml. Preferably, the pH is adjusted to approximately 8 to 9 with an appropriate basic solvent, such as 0.1M NaOH. A buffer, such as stock borate buffer, pH 8.5, is added to give final buffer molarity of 5 mM, pH 8.5. The volume is adjusted to give an appropriate substrate solution of tetrasaccharide, with a concentration such as 0.2–20 mg/ml.

Next, to the substrate solution is added an appropriately diluted mix of either or both of the chondroitinase proteins, such as 0.1–5 μg/ml, with a preferred dilution of 2 μg/ml. The preferred ratio of substrate solution to chondroitinase proteins is 6:1 (v/v). The assay solution is incubated at 10°–50° C., preferably 37° C., for an appropriate time, such as 15 minutes, and then chromatographed by GPC using an HPLC, such as a Shodex-OH pak KB-802.5 GPC-HPLC column (Shoko Co. Ltd., Tokyo, Japan). Other HPLC methods are also suitable, such as anion exchange, hydrophobic interaction, and reverse-phase.

The disaccharide product is detected and estimated by loading the digested substrate on a GPC-HPLC column such as described above. The mobile phase is 0.03% TFA in water. Other mobile phases can also be used, such as acetonitrile-water, or buffers like phosphate and borate. There is baseline separation of the unsaturated tetrasaccharide substrate and the disaccharide product. The relative amounts of the materials under these two peaks are estimated by a variety of conventional techniques, such as measuring the absorbance at a given wavelength, mass spectrometry, conductivity, refractive index and viscosity, and comparison to standards purified earlier and identified by TLC and other methods. It is often preferred to measure the absorbance at 232 nm.

Using GPC, the tetrasaccharide elutes before the disaccharide. The tetrasaccharide is shown to be stable during the several steps of the assay, such as adjustment of the pH to 8.5 with NaOH, and incubation for short durations (up to 30 minutes) at 37° C.

Even at high ratios of substrate to chondroitinase protein, such as 20,000:1 (w/w), the purified chondroitinase II protein converts the tetrasaccharide to disaccharide at close to linear rates, at least during the initial time points. The recombinant chondroitinase I protein is not able to effect this conversion. However, as expected, a co-purified mixture of chondroitinase I and chondroitinase II proteins (85:15 w/w) does catalyze this conversion. The rate of this conversion is proportionately slower than that seen for pure chondroitinase II protein, which is again as expected, in agreement with its lower content of the chondroitinase II protein.

When the concentration of chondroitinase proteins is increased one hundred fold (200:1 substrate:chondroitinase protein), both the pure chondroitinase II protein and the 85:15 co-purified protein mixture cause complete conversion to the disaccharide in 15 minutes. Even if this high concentration is used for recombinant chondroitinase I, no significant activity is detected. Thus, this in vitro assay provides a useful method for monitoring the conversion of the tetrasaccharide to the disaccharide, which is dependent only on the content of chondroitinase II. However, when the Proteus-derived chondroitinase I which contains a known contamination of the chondroitinase II protein (approximately 1 to 2%) is used alone, chondroitinase I does exhibit a detectable conversion even at this high purity.

Purification

Figure 9:
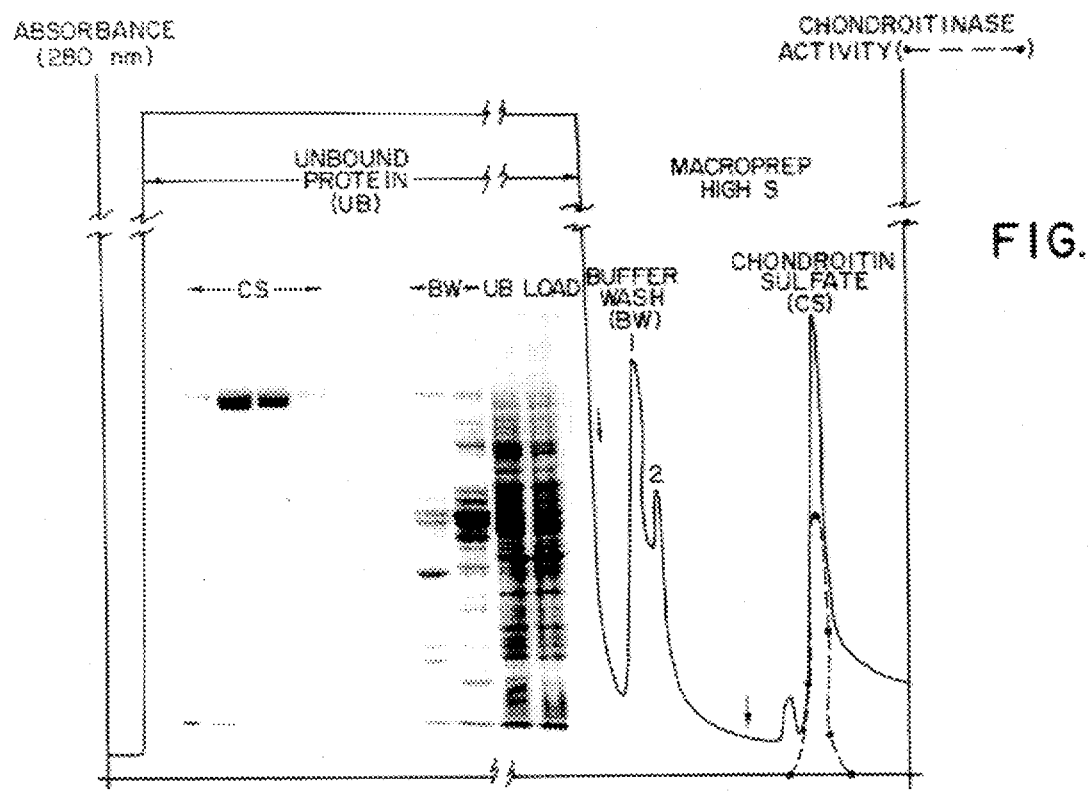
FIG. 9 is a graphic illustration of an initial step in the co-purification of chondroitinases I and II in which an induced *P. vulgaris* extract is fractionated using MacroPrep High S cation exchange chromatography. The graph (solid line) shows the absorbance at 280 nm of the column eluate (UB, unbound; BW, buffer wash; and CS, specific elution with chondroitin sulfate). The inset is an illustration of the SDS-PAGE profiles of the unbound, buffer wash, and chondroitin sulfate eluate fractions.

Although a variety of methods can be used to isolate and purify the native chondroitinase II protein, a preferred method will now be set forth. This method first involves the copurification of chondroitinase I and chondroitinase II from the crude extract of the *P. vulgaris* fermentation mash (See FIG. 9).

It is determined that the copurification process typically results in a weight/weight ratio of approximately 60% chondroitinase I:40% chondroitinase II, although ratios of up to approximately 80% chondroitinase I:20% chondroitinase II are also obtained. The copurified proteins are then separated from each other by additional process steps such as further cation exchange chromatography.

An affinity chromatography system is used for the copurification of the chondroitinase I and chondroitinase II proteins that recognize chondroitin sulfate. First, a cation exchange resin is used to bind the chondroitinase I and the chondroitinase II proteins from the crude extract of the *P. vulgaris* fermentation mash. Contaminating proteins are washed from the column and are not bound to the resin. The affinity elution of the chondroitinase I and chondroitinase II proteins is accomplished with a solution of chondroitin sulfate. The coeluted proteins contain contamination of chondroitin sulfate and its digestion products.

Final copurification occurs by loading the impure mixture on an anion exchange resin. The resin binds chondroitin sulfate, other proteins, DNA and endotoxins and digestion products, while the chondroitinase I and the chondroitinase II proteins flow through unbound. The final copurification, when done on a large scale, is accomplished using a resin which has been charged with nickel chloride and equilibrated. Most remaining contaminating proteins flow through while the two proteins of interest bind. The chondroitinase I and chondroitinase II proteins are then eluted from the resin. While nickel salts are preferred, other salts such as zinc, copper and iron are also acceptable.

The proteins are eluted from the *P. vulgaris* fermentation mash using a simple chromatographic system. Additionally, the proteins are purified and retain their biological activity without a loss in potency.

The resins used in this process are easily prepared and can be recycled by a simple process of regeneration with an acid, alkali cycle. Furthermore, the ion exchange resins are relatively inexpensive.

The copurified proteins are suitable for use in complete disinsertion of the vitreous body in ocular surgery. If desired, the copurified proteins can be separated from each other by additional process steps involving further cation exchange chromatography. The individually purified proteins can be used in ratios other than those obtained by the copurification procedure.

Specifically, the copurification of the two proteins is performed as follows. The induced *P. vulgaris* fermentation mash is centrifuged and the resulting pellet is suspended in pH 6.8 sodium phosphate buffer and then homogenized. The pH is most preferred in the range of 6.5 to 7.0. Also preferred is the range of 5.8 to 7.4. At a pH below 5.8, there is loss of activity due to precipitation of the proteins under the acidic conditions. The loss in activity is most significant at a pH below 5. Buffers other than phosphate can also be used. Preferably, the supernatant is adjusted to pH 6.8 using acetic acid and a conductivity of at least 3 milliSiemens/cm or lower. The appropriate conductivity is critical to achieve complete binding of the chondroitinase proteins to the subsequent cation exchange resin. It is determined in experiments that the conductivity must be below 3 milliSiemens/cm.

By doing these steps, the efficiency at which the chondroitinase I and chondroitinase II proteins bind to the cation exchange resin which follows in the next step is increased. Smaller amounts are bound up to a conductivity of about 4–5 milliSiemens/cm. Higher conductivities result in the majority of the proteins being lost in the unbound fraction.

The pH adjusted, clarified and homogenized extract is loaded onto a cation exchange resin support, Macro-Prep™ High S (Bio-Rad Laboratories, Melville, N.Y.). A preferred cation exchange resin is a high efficiency cation exchange resin which will allow a minimal amount of resin to be used. Among the charged support resin materials that are suitable for use in the present invention are other negatively charged groups. For example, carboxymethyl (CM) can be also used. Several available supports can be used: e.g., Macro-Prep™ which are acrylic supports, or other commonly-used supports like dextran, agarose, polyacrylamide, silica, or polymethacrylate, as long as they carry negative charges and are capable of binding to the positively charged proteins. The chondroitinase I and chondroitinase II proteins bind to the resin, while most of the protein contaminants flowthrough. The resin is washed with pH 6.8 sodium phosphate buffer to near zero absorbance at 280 nm and then is equilibrated with pH 8.3 sodium borate solution.

This pH adjustment is important to obtain an effective/specific elution in the next step. This pH is close to the optimal pH for chondroitinase activity. At this pH, there is a high degree of specific interaction between the chondroitinase proteins that are bound on the resin and the excess free substrate, causing the specific elution, while non-chondroitinase proteins (contaminants) remain bound. This pH is also close to the isoelectric point of the proteins, which allows for greater ease of elution. A pH of 8 to 9 can be used, although pH 8.3 to 8.5 gives the best results and is most particularly preferred. Other buffers in this pH range are also acceptable.

The affinity elution is accomplished with a 1% solution of chondroitin sulfate in water at a preferred pH range of 8.5 to 9. The efficiency decreases if the elution pH is below 7. The pH is adjusted with sodium hydroxide. Other alkalies can also be used. The concentration of the substrate can be as low as 0.2% and as high as 10%. However, a lower percentage results in lower yields (below 0.5%) and a higher percentage results in higher levels of contaminating proteins due to increased conductivity of the eluent. The recovery of chondroitinase activity is about 72%, with a purity of 90 to 98% of the proteins being a mixture of the chondroitinase I and chondroitinase II proteins. (See FIG. 9).

Although the pH of the chondroitin sulfate solution is adjusted, since there is no buffer in the solution (chondroitin sulfate is dissolved in deionized water), the pH is maintained close to the equilibrium pH of the resin (which is the borate buffer pH, used earlier before elution), in this case pH 8.3.

The elution using the substrate results in higher chondroitinase protein purity compared to that obtained using salt solutions. In addition, salt eluted proteins require an additional desalting/diafiltration step before the next ion exchange step, which is not required for the affinity eluted proteins. This is because the conductivities needed for salt elution are about 20 fold more than 1% chondroitin sulfate solution.

The affinity eluted protein pool is simply adjusted to a pH of 6.8 preferably with acetic acid and is loaded on an anion exchange resin support Macro-Prep™ High Q (Bio-Rad; Q stands for quaternary ammonium) or equally efficient resin. A preferred anion exchange resin is a high efficiency anion exchange resin which will allow an minimal amount of resin to be used. Other positively charged groups like DEAE can also be used.

Figure 10:
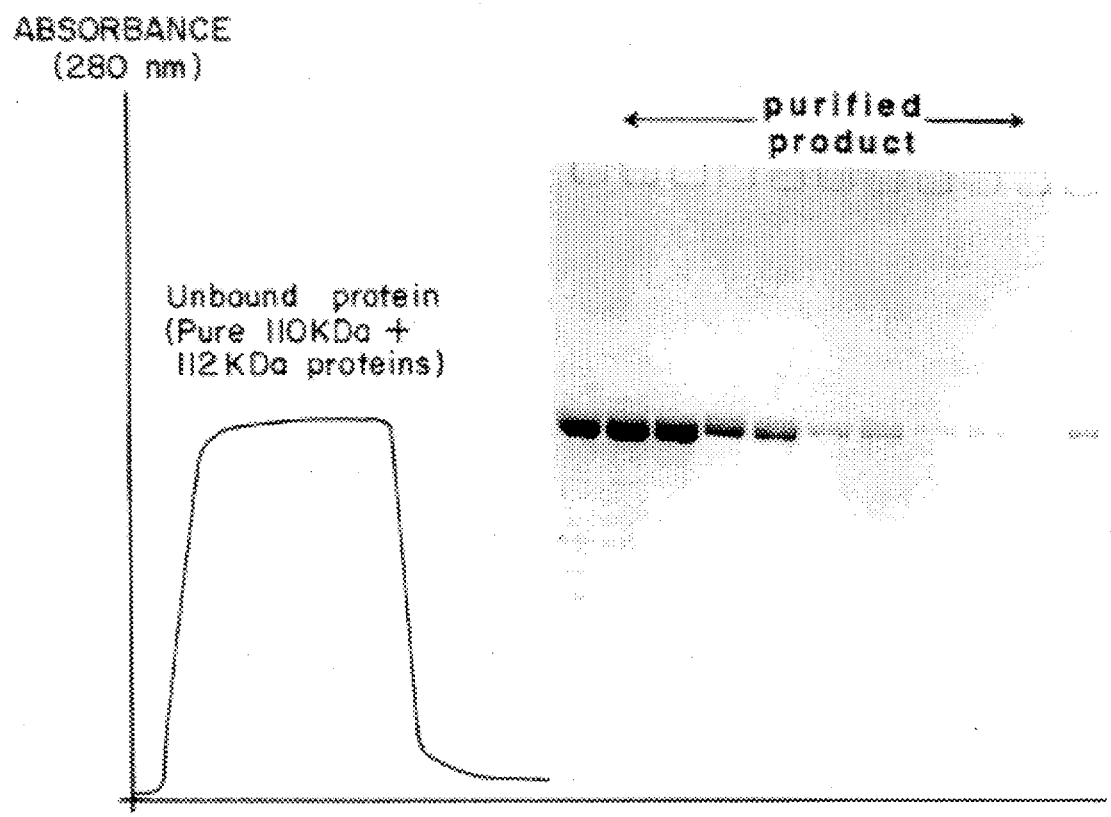

Both the chondroitinase I and chondroitinase II proteins are co-eluted from the column, and the chondroitin sulfate and its digestion products are bound to the resin along with other proteins, DNA, and endotoxins. The resin is not only capable of removing chondroitin sulfate and increasing the purity of the product, but is also very effective in removal of endotoxin. The recovery in this step is 86% and the protein purity of the chondroitinase I and chondroitinase II proteins is increased to 95–99%. (See FIG. 10).

On a 1000 liter fermentation scale, the protein purity of copurified chondroitinase I and II enzyme proteins after a sequential purification on a cation exchange column and a anion exchange column is less than that obtained under laboratory scale purifications. A third chromatography step using metal chelating affinity chromatography (MCAC) is used to improve purity of the proteins. The separation is based on differing abilities of proteins to interact with chelated metal attached to an insoluble support. Proteins bind mainly because of their content of histidine or cysteine. Varying the metal ions and the pH and salt concentration of the loading buffer establishes conditions under which the contaminating proteins will flow through, and only the chondroitinase I and chondroitinase II proteins bind to the charged resin. By eluting with 50 mM imidazole in 50 mM tris-acetate at pH 8 in the presence of 0.2M NaCl as the elution buffer, a protein purity of 98% is obtained without losing in vivo activity. Imidazole may be present in the protein eluted, and may be separated from the protein by dialysis or diafiltration against water or a buffer.

The copurified proteins can be separated from each other by additional process steps. The individually purified proteins could thereafter, be reformulated in ratios other than those obtained by the copurification procedure.

The eluate containing the copurified chondroitinase I and chondroitinase II proteins is adjusted to a pH of 6.8. The copurified proteins are subjected to cation-exchange chromatography on Macro-Prep™ High S column, pH 6.8. The column is washed with a borate buffer, pH 8.5. The two chondroitinase proteins are eluted from the column with a NaCl gradient of 0–150 mM in borate buffer. Alternatively, a single molarity solution of 50 mM NaCl in borate buffer is also equally effective. In each case, the chondroitinase I protein elutes in earlier fractions, separated from the chondroitinase II protein, which elutes in later fractions. (See FIG. 11). Amino-terminal sequencing of the purified chondroitinase I fractions yields a single sequence; and amino-terminal sequencing of the purified chondroitinase II fractions also yields a single, different sequence. Each protein is recovered at a purity of 98–99% and a yield of 85–95% from the copurified protein mixture.

Disinsertion and Therapeutic Compositions

The vitreous body is a connective tissue compartment which occupies four-fifths of the volume of the eye and provides structural and metabolic support for ocular tissues, while also assisting in the maintenance of intraocular pressure and allowing light to reach the retina. The vitreous body often forms secondary attachments to the retina at the border of degenerative or inflammatory lesions. In turn, these attachments form pivot points on the surface of the retina which often cause its detachment.

Vitrectomy is the surgical removal of a portion of the vitreous body and is indicated for the treatment or prevention of a variety of pathologic, operative or postoperative conditions which, if untreated, can result in blindness. It is preferred that vitrectomy be carried out using a method for selectively and completely disinserting the ocular vitreous body. The method takes advantage of the knowledge that a chondroitin sulfate-containing proteoglycan is involved in vitreoretinal adhesion and that compositions which act upon the proteoglycan will result in disinsertion of the vitreous body without deleterious effects upon the rest of the eye.

Testing of the isolated and purified native chondroitinase I and II proteins reveals that it is the combination of the two proteins which results in the complete disinsertion required for surgical vitrectomy, rather than either of the proteins individually.

One aspect of this invention comprises administering to the eye an effective amount of two chondroitinase enzymes, chondroitinase I and chondroitinase II, which degrade chondroitin sulfate glycosaminoglycan/proteoglycan that is localized specifically to sites of vitreoretinal adhesion. Chondroitin sulfate is a glycosaminoglycan which is attached to a larger molecular weight proteoglycan. Chondroitin sulfate is responsible for vitreoretinal adhesion, such that degradation of chondroitin sulfate results in complete disinsertion of the vitreous body.

Use of these two proteins provides for enzymatic disruption of the vitreoretinal interface, in particular, to enzymatic disinsertion (complete removal) of the vitreous body of the eye.

In vivo, the dose of the two chondroitinase proteins needed to achieve complete disinsertion of the vitreous body in the eye varies with the time of treatment. In general, the shorter the period of treatment, the larger the dose, with the limitation that the dose cannot be high enough to cause retinal or ciliary body toxicity. The treatment time can range from as short as one minute up to several hours.

Generally, a surgical or therapeutic composition contains between 1 and 10,000 units and (CI activity units) of a mixture of chondroitinase I and chondroitinase II proteins for selectively and completely disinserting the ocular vitreous body from the neural retina of the eye. Preferably, a surgical or therapeutic dosage would be between about 150 and about 1500 units. A unit is that quantity of protein that catalyzes the formation of 1 micromole of unsaturated disaccharide from chondroitin sulfate per minute at 37° C., pH 8.0. The dose is also calculated in terms of units of protein per milliliter of vitreous volume to be completely disinserted, and thus the dose can be as low as 0.05–0.1 of such units per ml.

It may be more convenient to refer to the activity of the proteins in terms of milligrams per milliliter of a pharmaceutically acceptable buffered solution. For chondroitinase I, 500 units/ml are equivalent to 1 mg protein/ml. A preferred dosage range is 1–10 mg total protein/0.4 ml buffered saline solution (BSS), with a particularly preferred dose of 4 mg total protein/0.4 ml BSS. In turn, the preferred ratios of proteins range from 90% chondroitinase I:10% chondroitinase II (w/w) to 60% chondroitinase I:40% chondroitinase II (w/w).

The chondroitinase proteins are preferably administered in a pharmaceutically acceptable buffered solution formed by mixing the concentrated proteins with a buffer solution. Any suitable buffer solution may be used, including sodium acetate, Tris, or a Balanced Salt Solution (Alcon, Fort Worth, Tex.). The proteins are effective at the pH range 4.5–9.0, preferably about pH 8.0. Therefore, the preferred pH range for buffered solutions of the proteins is approximately 7–8.

A typical formulation or dosage unit form includes a sterile lyophilized cake containing both of the copurified or isolated enzymes and a pharmaceutically acceptable excipient. Suitable excipients include, but are not limited to, citrate buffer and dextrose. A pharmaceutically acceptable diluent may also be added. A suitable diluent is a balanced salt, such as, for example, a balanced salt diluent containing sodium chloride, potassium chloride, calcium chloride, magnesium chloride, sodium acetate, sodium citrate, and water such as, for example BSS (Alcon Surgical, Inc. Storrs, Conn.).

The lyophilized cake typically includes the excipient, and typically is reconstituted in 0.5 to 2.0 ml volumes of diluent prior to use.

Suitable dosages can be determined by those skilled in the art, such as, for example by establishing a matrix of and subjects assigning a subject to each dosage.

A non-limiting example of a formulation is given in Table 2 below:

TABLE 2

SAMPLE FORMULATION

| Ingredient | Protein lyophilized (mg/vial) |
|---|---|
| Chondroitinase | a |
| Dextrose anhydrous, USP | 5.00 |
| Sodium citrate dihydrate, USP | 0.96 |
| Citric acid monohydrate, USP | 0.03 |
| Sodium hydroxide, NF | b |
| Water for injection | may be used | a adjustable to provide 3000 Units/vial, depending on the specific activity of the bulk material, contains 10% overage.
b added as required to adjust pH of final solution In vivo testing in monkeys demonstrates the therapeutic compositions. Monkeys are anesthetized and the two chondroitinase proteins are administered to the eye by means known in the art, such as intravitreal, subvitreal, sublenticular and posterior chamber administration. In one procedure, part of the vitreous body is removed by a vitrectomy instrument inserted through a first port in the eye. Light for the surgeon is provided by an endoilluminator inserted through a second port in the eye. The remainder of the vitreous body is removed by injecting the protein solution of this invention through a third port referred to as the infusion terminal. The solution diffuses through the vitreous body and the two chondroitinase proteins act to degrade the chondroitin sulfate which attaches the vitreous to the retina. After the degradation is complete, which can occur in as little as 15 minutes, the completely disinserted vitreous is removed by suction and the eye is flushed with a saline solution. A buffer solution under proper pressure is then administered through the infusion terminal. Over time, the body synthesizes the necessary molecules to essentially reconstitute the vitreous body.

The animals are sacrificed and the eyes are analyzed by such methods as visual examination, histology and pathology, sonography, transmission electron microscopy, and the use of anti-chondroitin sulfate antibodies. Where the disinsertion is incomplete, such as when only chondroitinase I is administered, some of the vitreous body in the region of the vitreous base is large enough that it can be grasped by forceps. The selectivity of the two chondroitinase proteins is demonstrated in that, when complete disinsertion is achieved, no damage to the retina is visible.

A series of monkey vitrectomy experiments was performed, testing various purified Proteus chondroitinase preparations. These experiments are summarized as follows. Monkeys receiving compositions containing both chondroitinase proteins, isolated and purified from one of several fermentation batches, had vitreal disinsertion. A batch which was fractionated to remove the chondroitinase II protein caused incomplete disinsertion. Histology of the tissue showed that undigested chondroitin sulfate was present if chondroitinase II was not included in the dose administered.

When purified chondroitinase II protein was added back to the fractionated batch lacking chondroitinase II (to about 12% of total protein by weight), a successful disinsertion was achieved.

Based on evaluation of these preparations by surgical criteria, it is concluded that the chondroitinase II protein plays an essential role in effecting complete vitreal disinsertion. Without the inclusion of chondroitinase II, chondroitinase I alone was ineffective in achieving complete vitreal disinsertion in the animal model.

DESCRIPTION OF THE PREFERRED EMBODIMENTS

The following examples illustrate the invention without limitation

EXAMPLE 1

Purification

A 10 L volume of induced *P. vulgaris* mash was centrifuged at 6,400 g for 20 minutes. The pellet was resuspended in 10 mM sodium phosphate buffer at pH 6.8 and then was centrifuged again. The washed pellet was resuspended in the above buffer and homogenized three times through a Gaulin homogenizer at ~9000 p.s.i., three times. The homogenate (1.8 liters) was centrifuged at 17,700 g for 1 hour. Most of the supernatant (1.4 liters of 1.7 liters) was adjusted to a pH of 6.8 using 1M acetic acid and to a conductivity of 3 milliSiemens/cm by dilution with deionized water. Both of these steps ensured the efficient binding of the chondroitinase proteins to the cation exchanger that follows.

The adjusted, clarified, homogenate (2.4 liters containing 62.4K units of chondroitinase I enzyme activity (EC #4.2.2.4)) was loaded on a Macro-Prep™ High S cation exchange column (Bio-Rad, Melville, N.Y.) of bed volume 340 ml, at a load of 184 units/ml resin. The chondroitinase proteins bound to the resin while the majority of contaminating proteins flowed through, unbound. The column was washed with ~4 bed volumes of 10 mM sodium phosphate buffer pH 6.8 to bring the absorbance at 280 nm close to baseline. The resin was equilibrated with ~6 bed volumes of 40 mM sodium borate at pH 8.3.

The affinity elution was performed using a 1% solution of chondroitin sulfate (Fluka Biochemicals) in water, adjusted to a pH of about 8.5 to 9 with NAOH. The two proteins were specifically eluted as a sharp peak, in about half the bed volume. The recovery of chondroitinase activity was 72%, with 96 to 98% of the proteins being a mixture of the chondroitinase I and the chondroitinase II proteins.

The affinity eluted protein pool was adjusted to pH 6.8 with acetic acid and was loaded on a Macro-Prep™ High Q anion exchange resin (Bio-Rad, Melville, N.Y.) of bed volume 85 ml, equilibrated at pH 6.8. Both the chondroitinase proteins eluted unbound in the flow through, while the chondroitin sulfate and its digestion products were bound to the High Q resin. The removal of chondroitin sulfate and its degradation products was confirmed by sulfate microanalysis of the load and the flow-through. By this step, 99.6% of the sulfate in the load was removed and the remaining 0.4% could be accounted for primarily by partial oxidation of the sulfur within methionines in the proteins during ashing. In addition to the removal of chondroitin sulfate and its products, there was an increase in purity to about 98–99%. The recovery in this step was 38.3K units of chondroitinase (86%).

EXAMPLE 2
Purification

A 2.6 L volume of induced *P. vulgaris* mash was centrifuged at 6,400 g for 20 minutes. The resulting pellet was resuspended in 350 ml of 10 mm sodium phosphate buffer pH 6.8 and was centrifuged again. The pellet (142 g) was resuspended in 350 ml of deionized water and was homogenized for three passes at about 10,000 p.s.i.. The homogenate was clarified by centrifugation at 17,700 g for 1 hour, and clarified homogenate was pH adjusted to 6.8 with 1M acetic acid and diluted to a conductivity of 3 milliSiemens/cm with deionized water. The adjusted clarified homogenate (16.2K units in 850 ml) was loaded onto a Macro-Prep™ High S column (Bio-Rad, Melville, N.Y.) of bed volume of 105 ml (154 units/ml resin). The column was then washed with about 2 bed volumes of 10 mM sodium phosphate buffer pH 6.8, followed by about 8 bed volumes of 40 MM sodium borate buffer of pH 8.3. The chondroitinase proteins were next co-eluted with 1% chondroitin sulfate in deionized water adjusted to pH-9 with 1M NAOH, at a purity of about 96–98% and a recovery of 88%. This eluted fraction was then adjusted to pH 6.8 with 0.1M acetic acid and loaded on a MacroPrep"' High Q column (Bio-Rad, Melville, N.Y.) of bed volume 10.5 ml, equilibrated in 10 MM sodium phosphate buffer pH 6.8. The chondroitinase proteins were collected in the flow-through at a recovery of 95% and a purity of about 98 to 99%. The overall recovery from mash to purified proteins was 73%.

EXAMPLE 3
Purification

A 1000 L *P. vulgaris* fermentation with a final chondroitinase potency of 7.9 u/ml was produced. The fermentation was diluted with 2000 L of deionized water and was cooled to 12° C. The diluted mash was centrifuged at a flow rate to 80 L/minute to separate the fermentation broth from the cell solids. The wet mash solids were diluted with deionized water prior to homogenization. The 200 L of wet cells were homogenized in three passes using the Gaulin M3 Homogenizer at 8000 psi and a flow rate of 5 L/minute. The homogenate was diluted with deionized water prior to clarification to lower the conductivity further and then was centrifuged to remove cell debris. The clarified homogenate was diluted further to lower the conductivity below 3 milliSiemens/cm.

This material (570 L) was loaded onto a 24 L Macro-Prep™ High S column cation exchange (Bio-Rad, Melville, N.Y.) that had been equilibrated with 10 mM sodium phosphate pH 6.8. The flow rate was 1 L/minute. After loading, the resin was washed with about 3 bed volumes of 10 mM phosphate pH 6.8 and then was equilibrated with 40 mM borate pH 8.3 (5 bed volumes) until the appropriate pH for elution was achieved. A 15% portion of the loaded chondroitinase I activity did not bind to the resin and was detected in the flow through. Elution was carried out with 1% chondroitin sulfate at pH 8.9 and was monitored by absorbance at 280 After 9 L eluted and the absorbance began to increase, fractions of 5 L were collected. Each fraction was analyzed by SDS-PAGE and enzyme activity assay. The desired fractions were combined, resulting in a recovery of 5.35 million units and a step yield of 82%. Purity of chondroitinases I and II by SDS-PAGE was 81%.

The pH of the High S eluate was adjusted to 6.9 using 1M acetic acid prior to loading onto a 3 L Macro-Prep™ High Q column (Bio-Rad, Melville, N.Y.). The feed was loaded onto the resin at 1780 u/ml resin at a superficial linear velocity of 100 cm/hr. The chondroitinase proteins were recovered in the flow-through, which was collected as one pool. Step yield from the anion exchange column was 96%. The flow through (9.95 L containing 5.14 million units) was concentrated by ultrafiltration, using a 30K spiral wound cartridge, to about 2 L before diafiltration against Water for Injection. The retentate was then lyophilized. Purity of the final lyophilized powder was 94% by area % stain from SDS-PAGE.

EXAMPLE 4
Purification

A chondroitinase preparation resulting from a 10 L fermentation was used. The mash was processed as described in Example 1. Side fractions containing the contaminating proteins were included to simulate the low purity obtained on large scale. This allowed for a preparation after the High Q step that was similar to that obtained on the large scale (i.e., about 90% purity). This became the starting preparation to standardize the third, metal affinity purification step. The purity of the eluate from the Macro Prep High Q by SDS-PAGE was approximately 90%.

For the final metal affinity purification step, a chelating Sepharose™ (Pharmacia LKB Biotechnology, Inc., Piscataway, N.J.) column with a bed volume of 23 ml was prepared. The resin was washed with deionized water, then charged with one bed volume of 0.1M nickel chloride. The resin was washed with water to remove unbound nickel and then was equilibrated with the loading buffer (50 mM Tris-acetate pH 8.0, 0.2M NACl). To the eluate from the High Q column, which contained low concentration of phosphate, 1M Tris-acetate (pH 8) and 2M NaCl were added to make a protein solution with the final concentration of the loading buffer. The prepared sample was loaded onto the column at 430 u/ml resin. The flow rate was 150 ml/hr corresponding to a superficial linear velocity of 75 cm/hr. After the sample was loaded, the resin was washed with loading buffer (approximately 5 bed volumes). Analysis of the flow through by activity assay and SDS-PAGE showed that most of the contaminating proteins, but less than 0.5% of the loaded activity, were recovered in this fraction. Elution with 50 mM imidazole in starting buffer resulted in the elution of a single protein peak, collected in fractions which were analyzed by SDS-PAGE. The desired fractions were combined resulting in a yield of 89% and an estimated chondroitinase purity of 96–98%.

EXAMPLE 5
Purification

Purification was repeated under the same conditions as Example 4, but with an increased load (900 u/ml resin). Yield off the column was 75%, and chondroitinase purity by SDS-PAGE was 98%. The eluate was concentrated, diafiltered into water, and lyophillzed.

EXAMPLE 6
Purification

A 1000 L induced *P. vulgaris* fermentation with a potency of 7.5 u/ml mash was initially processed as described in Example 2. Chondroitinases I and II purity of the eluate from the Macro-Prep™ High Q (Bio-Rad, Melville, N.Y.) column by SDS-PAGE was 83.9%. A column with a diameter of 18 cm was packed with approximately 9 L of Chelating Sepharose'm Fast Flow resin (Pharmacia LKB Bioteclmoloy, Inc., Piscataway, N.J.). After the resin had been washed with water, it was charged with nickel chloride and was equilibrated with 50 mM Trisacetate buffer (pH 8) containing 0.2M NaCl. The High Q flow-through was adjusted to a final concentration of 50 mM Trisacetate pH 8 and 0.2M NaCl. The prepared feed was loaded onto the column at 600 u/ml resin at a flow rate of 19.2 L/hour corresponding to a superficial linear velocity of 75 cm/hour. The chondroitinase proteins were eluted from the column with an elution buffer, made of 50 mM imidazole in starting buffer. Step yield was 89% and the purity of chondroitinases I and II was increased from 83.9% to 96.4%.

Figure 3:
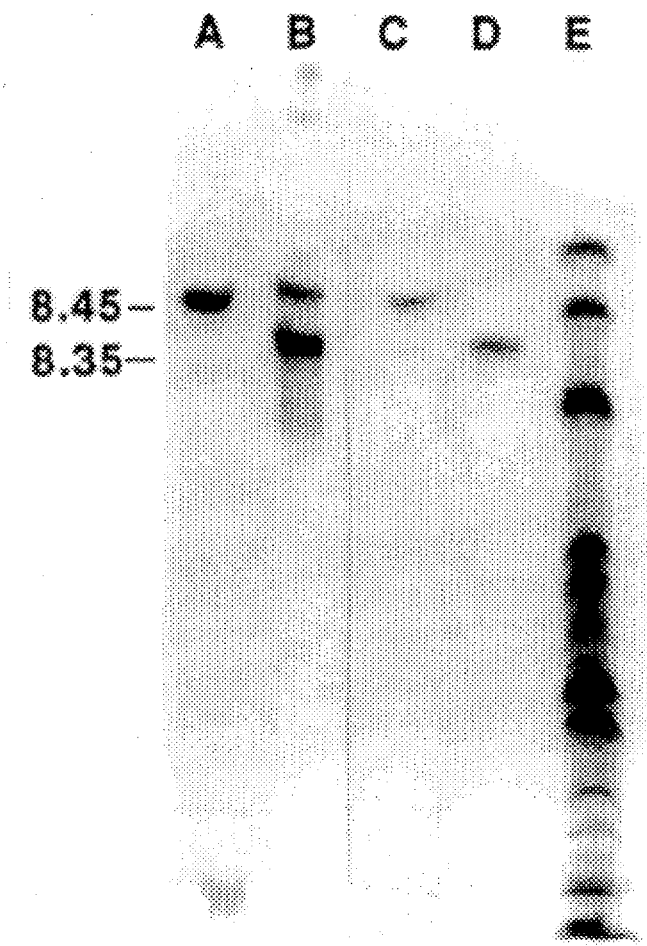
FIG. 3 is an illustration of gel isoelectric focusing of pure chondroitinase II (Lanes A and C); co-purified chondroitinases I and II (Lane B); and purified chondroitinase I (Lane D).

EXAMPLE 7
Isolation Of The Tetrasaccharide Substrate For Use In The Assay Of Chondroitinase Activity 5.8 mg of purified native chondroitinase I were added to 8 g chondroitin sulfate (Fluka Chemicals, Buchs, Switzerland) in 600 ml of water, pH adjusted to 8.8, with 0.1M NaOH. Alternatively, *E. coli*-expressed recombinant chondroitinase I, available by expression of ATCC 69234, was used. The mixture was incubated at 37° C. for 3 hours and was concentrated by partial lyophilization to 55 ml. The concentrate was diluted to 1:1 (v/v) with 0.1% TFA in water. The chondroitinase I digested chondroitin sulfate into products that were recovered as four peaks from a gel permeation column (Spectra/Gel TAc, Spectrum Medical Industries Inc., Los Angeles, Calif.) by eluting with 0.1% TFA as a solvent. The first peak, designated I, was a small peak eluting at the void volume, consisting of chondroitinase I, and did not contain any reducing sugar. The second peak, designated II, comprised two distinct components designated IIa and IIb. IIa contained the ⅓ R.F. sugar in an enriched form, while IIb was oversulfated disaccharide. The third peak, designated III, which was the largest, eluted close to the bed volume and consisted of almost pure disaccharide. This GPC is depicted in FIG. 3 (FIG. 019) (peak III is labelled IIIa and IIIb). Peak IV consisted of non-sugar components.

The peaks from the GPC were analyzed by TLC and the tetrasaccharide of interest (Peak IIa) were found to elute free of the major component of the digest, the disaccharides. The fractions were lyophillzed to remove the TFA/water and were analyzed. Approximately one-fourth of the digested material was composed of the tetrasaccharide, as a white crystalline salt-free powder, at a yield of approximately 200 mg and a purity of approximately 95%.

EXAMPLE 8
In vitro Assay For The Activity Of The Chondroitinase II Protein In Converting The Tetrasaccharide To The Disaccharide The assay was conducted as follows. First, the tetrasaccharide substrate was prepared in a suitable solution. Pure tetrasaccharide was dissolved in water to about 2.5 mg/ml, and the pH was adjusted to approximately 8 to 9 with 0.1M NaOH. Stock borate buffer, pH 8.5, was added to give final molarity of 5 mM, pH 8.5. The volume was adjusted to give a 2 mg/ml solution of tetrasaccharide.

Next, to 60 μL of the substrate solution were added 10 μL of an appropriately diluted mix of either or both of the chondroitinase proteins, such as 0.1–5 μg/ml, with a preferred dilution of 2 μg/ml. The assay solution was incubated at 37° C. for 15 minutes, and 20 μl of digested substrate were then chromatographed on GPC using an HPLC, with a Shodex-OH pak KB-802.5 GPC-HPLC column (Shoko Co. Ltd., Tokyo, Japan). The mobile phase was 0.03% TFA in water. There was baseline separation of the tetrasaccharide substrate and the disaccharide product, where the two peaks were estimated by absorbance at 232 nm and comparison to standards purified earlier and identified by TLC.

Under these conditions of GPC, the tetrasaccharide eluted at about 5.2 ml, while the disaccharide eluted at about 6.3 ml, where the bed volume was about 10 ml. The tetrasaccharide was shown to be stable during the several steps of the assay, such as adjustment of the pH to 8.5 with NaOH, and incubation for short durations (up to 30 minutes) at 37° C. The assay time chosen was 15 minutes, which allowed for continuous loading of freshly incubated reactions, since the run time was 12 minutes.

Even at a ratio of substrate to chondroitinase protein of 20,000:1 (w/w), the purified chondroitinase II protein converted the tetrasaccharide to disaccharide at close to linear rates, at least during the initial time points. The recombinant chondroitinase I protein was not able to effect this conversion. However, as expected, a copurified mixture of chondroitinase I and chondroitinase II proteins (85:15 w/w) did catalyze this conversion. The rate of this conversion was much slower than that seen for pure chondroitinase II protein, which is again as expected, in agreement with its lower content of the chondroitinase II protein.

When the concentration of chondroitinase proteins was increased one hundred fold (200:1 ratio), both the pure chondroitinase II protein and the co-purified protein mixture caused complete conversion to the disaccharide. Even if this high concentration were used for recombinant chondroitinase I, no significant activity was detected. However, when the Proteus-derived chondroitinase I which contained a known contamination of the chondroitinase II protein (approximately 1 to 2%) was used alone, it did exhibit a partial conversion at this high ratio. Thus, this in vitro assay provides a useful method for monitoring the conversion of the tetrasaccharide to the disaccharide by chondroitinase II.

EXAMPLE 9
Vitreal Disinsertion In Monkeys

A series of monkey vitrectomy experiments was performed, testing various purified Proteus chondroitinase preparations. Healthy monkeys were divided into five groups. Four groups received a dose of 4 mg total chondroitinase protein in 0.4 ml BSS as follows: Group 1 received chondroitinase I alone; Group 2 received chondroitinase II alone; Group 3 received a 60:40 (w/w) mixture of chondroitinase I and chondroitinase II; and Group 4 received an 88:12 (w/w) mixture of chondroitinase I and chondroitinase II. A fifth group, Group 5, used as a negative control, received 0.4 ml BSS only.

The monkeys were anesthetized and part of the vitreous body was removed by a vitrectomy instrument inserted through a first port in the eye. Light for the surgeon was provided by an endoilluminator inserted through a second port in the eye. The remainder of the vitreous body was removed by injecting the protein solution through a third port referred to as the infusion terminal. After the degradation, if any, was complete (15 minutes), the animals were sacrificed and the eyes were analyzed by such methods as visual examination, histology and pathology, sonography, transmission electron microscopy, and the use of anti-chondroitin sulfate antibodies.

The results are illustrated in Table 3 below:

TABLE 3

| Group 1 | Incomplete disinsertion |
| Group 2 | No disinsertion |
| Group 3 | Complete disinsertion |
| Group 4 | Complete disinsertion |
| Group 5 | No disinsertion |

All patents, applications, articles, publications, and test methods mentioned herein are hereby incorporated by reference.

Many variations of the present invention will suggest themselves to those skilled in the art in light of the above detailed description. Such obvious variations are within the full intended scope of the appended claims.

We claim:

1. An isolated, purified protein consisting of the sequence of SEQ ID NO:2, wherein said protein having an amino acid sequence has chondroitinase II activity.

2. An isolated, purified protein having Protein vulgaris chondroitinase II activity, wherein said protein has an isoelectric point of approximately 8.4–8.45 and an apparent molecular mass of 112 kDa when electrophoresed in a 4 to 20% gradient acrylamide gel in 25 mM tris/192 mM glycine buffer at pH 8.5 in the presence of about 0.1% (w/v) SDS.

3. An isolated, purified protein Protein vulgaris having chondroitinase II activity, wherein said protein corresponds to the upper band of the doublet of FIG. 2, Lane D.

4. An isolated, purified protein having *Proteus vulgaris* chondroitinase II activity, which in combination with chondroitinase I selectively and completely disrupts vitreoretinal adhesion by digesting chondroitin sulfate proteoglycan localized specifically to sites of said adhesion.

* * * * *